United States Patent
Matsushige et al.

(10) Patent No.: US 8,497,312 B2
(45) Date of Patent: *Jul. 30, 2013

(54) ONE-PACKAGE DENTAL ADHESIVE COMPOSITION

(75) Inventors: Koji Matsushige, Tsukuba (JP); Makoto Oguri, Tsukuba (JP); Shizuka Shimizu, Tsukuba (JP); Takeshi Suzuki, Sakuragawa (JP)

(73) Assignee: Tokuyama Dental Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/276,585

(22) Filed: Nov. 24, 2008

(65) Prior Publication Data

US 2009/0076189 A1    Mar. 19, 2009

Related U.S. Application Data

(63) Continuation-in-part of application No. PCT/JP2007/061148, filed on May 25, 2007.

(30) Foreign Application Priority Data

May 26, 2006 (JP) ................................ 2006-147203
Sep. 5, 2006 (JP) ................................ 2006-239951
Oct. 18, 2006 (JP) ................................ 2006-284322

(51) Int. Cl.
*A61K 6/08* (2006.01)
*A61K 6/00* (2006.01)

(52) U.S. Cl.
USPC ........................... 523/116; 523/118; 523/120

(58) Field of Classification Search
USPC ............................................... 523/120, 118
See application file for complete search history.

(56) References Cited

U.S. PATENT DOCUMENTS

| | | | |
|---|---|---|---|
| 5,171,763 A | 12/1992 | Ohno et al. | |
| 5,556,897 A | 9/1996 | Honda et al. | |
| 6,191,190 B1 * | 2/2001 | Blackwell et al. | 523/115 |
| 6,583,197 B1 * | 6/2003 | Kouro et al. | 522/84 |
| 2004/0077746 A1 * | 4/2004 | Takeshita et al. | 523/116 |
| 2005/0176844 A1 * | 8/2005 | Aasen et al. | 523/118 |
| 2006/0069181 A1 * | 3/2006 | Thalacker et al. | 523/116 |

FOREIGN PATENT DOCUMENTS

| | | |
|---|---|---|
| JP | 4-214708 A | 8/1992 |
| JP | 6-009327 A | 1/1994 |
| JP | 6-024928 A | 2/1994 |
| JP | 10-236912 A | 9/1998 |
| JP | 10236912 A * | 9/1998 |
| JP | 11-130465 A | 5/1999 |
| JP | 2001-072523 A | 3/2001 |

OTHER PUBLICATIONS

English machine translation of JP Patent Pub No. 10-236912, Oguri et al, Sep. 8, 1999.*
English machine translation of JP Patent Pub No. 10-236912, Oguri et al, Sep. 8, 1998.*
English machine translation of JP 10-236912 A, Oguri et al, Sep. 8, 1998.*
English machine translation or JP 10-236912 A, Oguri et al, Sep. 8, 1998.*
Form PCT/ISA/210 (International Search Report) dated Aug. 28, 2007.
Akishi Arita, GC adhesive technology, Adhes Dent. pp. 31-38 vol. 22 No. 1 2004.

* cited by examiner

*Primary Examiner* — Peter F Godenschwager
*Assistant Examiner* — David Karst
(74) *Attorney, Agent, or Firm* — Buchanan Ingersoll & Rooney PC

(57) ABSTRACT

An adhesive composition comprising (A) a polymerizable monomer component containing not less than 5% by mass of an acidic group-containing polymerizable monomer, (B) a polyvalent metal ion-eluting filler, (C) a volatile organic solvent, and (D) water, wherein the polyvalent metal ion-eluting filler (B) is blended in such an amount that the amount of the polyvalent metal ions eluted out from the filler becomes 1.0 to 7.0 meq per gram of the polymerizable monomer component (A), the volatile organic solvent (C) is blended in an amount in a range of 30 to 150 parts by mass per 100 parts by mass of the polymerizable monomer component (A) and so as to satisfy 20·X parts by mass or more (X is a number representing the amount of elution of the polyvalent metal ions), and the water (D) is blended in an amount of 3 to 30 parts by mass per 100 parts by mass of the polymerizable monomer component (A). The composition maintains a large strength of adhesion to the teeth, can be preserved in the form of one package, and can be used as a material for pre-treating the teeth and as a dental adhesive.

5 Claims, No Drawings

ONE-PACKAGE DENTAL ADHESIVE COMPOSITION

TECHNICAL FIELD

This invention relates to a one-package dental adhesive composition used in the field of dental treatment. More specifically, the invention relates to a one-package dental adhesive composition which is used as a dental adhesive for adhering a composite resin (restorative filled in the cavity of a tooth) or a bracket for correction to the dentin or is used as a material for pre-treating the dentin prior to using the adhesive.

BACKGROUND ART

A tooth damaged by decaying, etc. can be restored by using a dental restorative called composite resin that contains a polymerizable monomer such as a methacrylate compound and a filler as chief components. In recent years, however, a photocurable composite resin blended with a photopolymerization initiator has been widely used since it can be used requiring simple operation. The composite resin is, usually, filled in the cavity of a tooth and is, thereafter, cured by polymerization. However, the composite resin by itself has no adhering property to the teeth and, therefore, a dental adhesive is used in combination with the composite resin. The adhesive must exhibit an adhesive strength large enough to overcome the internal stress that generates accompanying the curing, i.e., to overcome the tensile stress that occurs on the interface between the teeth and the composite resin. Otherwise, the composite resin may peel off after used for extended periods of time under severe oral environment and, besides, a gap may develop in the interface between the teeth and the composite resin permitting germs to infiltrate to adversely affect the dental pulp.

A bracket for correcting irregular teeth, too, is adhered to the teeth by using the dental adhesive. The adhesive for the bracket, too, has been replaced by the photocurable adhesive owing to its simplicity of use. The photocurable adhesive for the bracket has an advantage of excellent operability in that the adhesive can be photocured and adhered at any timing after the bracket has been positioned on the tooth surface. A generally employed method of adhesion comprises applying the adhesive for the bracket onto the predetermined surface of the bracket, and closely adhering the applied surface onto the tooth surface followed by photocuring.

The dental adhesive used for the composite resin or the bracket contains chiefly an acidic group-containing polymerizable monomer, a polymerizable monomer and a polymerization initiator as constituent components involving, however, a problem in that none of them can adhere to the teeth to a sufficient degree. In order to firmly fix the composite resin or the bracket to the dentin, therefore, the dentin has, usually, been pre-treated through two steps as described below prior to applying the adhesive for the composite resin or the adhesive for the bracket:

(1) Hard tooth is etched by applying an aqueous solution (etching agent) of an acid such as phosphoric acid, citric acid or maleic acid to the surface of the tooth; and (2) After etching, a solution (permeation accelerator, also called primer) containing an amphipatic monomer such as hydroxyethyl methacrylate (HEMA) and an organic solvent as chief components is applied to have the permeation accelerator permeate into the teeth.

The hard tissue of a tooth consists of an enamel and a dentin. Clinically, therefore, the adhesion must be effected to both of them. In general, the adhesion to the enamel is said to be a macroscopic mechanical fitting in which the adhesive permeates and cures in a coarse surface formed by deliming with an acidic aqueous solution whereas the adhesion to the dentin is said to be a microscopic mechanical fitting in which the adhesive permeates and cures among the fine gaps of spongy collagen fiber exposed on the surface of the tooth due to deliming. Here, however, the adhesive does not permeate into the collagen fiber so easily as into the surface of the enamel. Therefore, the etching is effected to improve adhesion to the enamel and, thereafter, the permeation treatment is effected by using the permeation accelerator (primer) to improve adhesion to the dentin.

According to the prior art as described above, the pre-treatment had to be effected in two steps prior to applying the dental adhesive in order to attain favorable adhesion to both the enamel and the dentin requiring, however, a cumbersome operation.

In order to reduce the complexity of operation, there has already been known a primer composition having both the deliming function (etching function) for the enamel and the dentin, and permeation property to the dentin (see, for example, patent document 1 and patent document 2).

Patent document 1: JP-A-6-9327
Patent document 2: JP-A-6-24928

That is, the above primer composition contains, as chief components, a polymerizable monomer having an acidic group such as phosphoric acid group or carboxylic acid group exhibiting teeth-deliming property as well as affinity to the dentin, and water which is necessary for deliming the teeth. The primer composition has self-etching property as well as permeation property to the dentin, and is capable of effecting both the etching and the permeation acceleration treatment to the dentin by using an acidic aqueous solution in one step of pre-treatment. In particular, the primer composition of the patent document 2 is blended with a polyvalent metal compound that elutes out polyvalent ions, such as an iron compound, and makes it possible to obtain a particularly high adhesive strength.

The above permeation accelerator or the primer composition itself is not, usually, blended with the polymerization initiator. At the time when the adhesive for the composite resin or the adhesive for the bracket applied thereon undergoes the photocuring reaction, however, radicals formed by the adhesive cause the polymerizable monomer contained in the permeation accelerator or in the primer composition to be cured by polymerization. Therefore, the adhesive is firmly adhered to the tooth.

The applicant has proposed a dental adhesive that strongly adheres to both the enamel and the dentin through a simple operation without requiring the pre-treatment (see patent document 3).

Patent document 3: JP-A-10-236912

The above dental adhesive contains, as part of the polymerizable monomer, water necessary for teeth-deliming and the polymerization initiator in addition to the acidic group-containing polymerizable monomer used in the above primer composition, and is, further, blended with a filler (e.g., fluoroaluminosilicate glass) having polyvalent metal ion-eluting property. That is, the dental adhesive has the same functions (function for teeth-deliming and function for accelerating the permeation into the dentin) as those of the above-mentioned primer composition. At the time of curing, further, the dental adhesive induces ionic crosslinking due to the action of the acidic group-containing polymerizable monomer, water and polyvalent metal ion-eluting filler in addition to the radical polymerization of the polymerizable monomer, strongly adhering to both the enamel and the dentin due to the synergistic action of the radical polymerization and the ionic crosslinking. As a result, the composite resin can be firmly adhered thereon.

DISCLOSURE OF THE INVENTION

However, the primer composition disclosed in the above patent document 1 is not still satisfactory from the standpoint of maintaining a high adhesive strength. Therefore, a higher adhesive strength is desired from the standpoint of fixing the dental adhesive to the surface of the tooth maintaining a large strength, the dental adhesive being used for fixing, for example, the composite resin and the bracket for correction.

The primer composition of the patent document 2 and the adhesive of the patent document 3 utilizing the ionic crosslinking are capable of improving the strength of adhesion of the composite resin and the bracket for correction to the tooth accompanied, however, by a problem of poor preservation stability.

That is, the polyvalent ionic metal compound having a property of eluting polyvalent ions and the filler are gelled if they are mixed with the acidic group-containing polymerizable monomer and are preserved in the form of one package. So far, therefore, it was necessary to prepare two solutions, i.e., a solution containing the acidic group-containing polymerizable monomer and another solution containing the above metal compound and the filler, which were preserved in the form of two packages, and these two liquids were mixed together just before being used by a dentist for the clinical treatment. Mixing of liquids at the time of use was a very cumbersome work for the dentist. Besides, the mixing conditions such as the mixing operation and the mixing time were inevitably dispersed to some extent depending on the persons who mix them together and, therefore, a certain degree of skill was necessary.

It is, therefore, an object of the present invention to provide a one-package dental adhesive composition which contains an ion-eluting polyvalent metal component, maintains a large adhesive strength, can be preserved in the form of one package, and can be used as a pre-treating material having etching capability for the dentin and infiltration acceleration property for the dentin and, particularly, can be used as a pre-treating material for the composite resin or for the adhesive for the correction bracket.

Another object of the present invention is to provide a one-package dental adhesive composition which can be used as a dental composition for the composite resin or for the correction bracket without requiring the treatment by using a pre-treating material, and can be preserved in the form of one package.

The present inventors have conducted keen study concerning dental adhesive compositions containing a compound having a property of eluting polyvalent ions, and have discovered the fact that a one-package dental adhesive composition can be obtained by using a volatile water-soluble organic solvent as a diluting solvent and by selecting the amount of the polyvalent metal ions eluted from the polyvalent metal ion-eluting filler and the amount of the water-soluble organic solvent so as to satisfy predetermined conditions, the one-package dental adhesive composition exhibiting not only a large adhesive strength but also excellent preservation stability, without requiring the operation of mixing two liquids together at the time of use, and capable of being preserved in the form of one package, and have thus completed the invention.

According to the present invention, there is provided a one-package dental adhesive composition comprising:

(A) a polymerizable monomer component containing not less than 5% by mass of an acidic group-containing polymerizable monomer;
(B) a polyvalent metal ion-eluting filler;
(C) a volatile water-soluble organic solvent; and
(D) water;
wherein the polyvalent metal ion-eluting filler (B) is blended in such an amount that the amount of the polyvalent metal ions eluted out from the filler becomes 1.0 to 7.0 meq per gram of the polymerizable monomer component (A);
the volatile organic solvent (C) is blended in an amount in a range of 30 to 150 parts by mass per 100 parts by mass of the polymerizable monomer component (A) satisfying a condition expressed by the following formula (I):

$$\alpha \geq 20 \cdot X \qquad (I)$$

wherein
 α is the amount of the water-soluble organic solvent (C) blended per 100 parts by mass of the polymerizable monomer component (A),
 X is a number representing the amount of the polyvalent metal ions eluted out from the polyvalent metal ion-eluting filler (B) or the amount (meq) thereof per gram of the polymerizable monomer component (A), and
 water (D) is blended in an amount of 3 to 30 parts by mass per 100 parts by mass of the polymerizable monomer component (A).

The one-package dental adhesive composition of the invention has an excellent function for teeth-deliming and an excellent function for accelerating the permeation into the tooth (particularly, dentin) and, therefore, can be used as a teeth pre-treating material for effecting the pre-treatments in one step, i.e., a step of etching prior to applying the dental adhesive and a step of accelerating the permeation. Upon blending (E) a photopolymerization initiator, further, the one-package dental adhesive composition can be directly used as the dental adhesive without requiring the pre-treatment by using the teeth pre-treating material.

In the one-package dental adhesive composition of the invention, it is desired that:
(1) a polyvalent metal ion non-releasing inorganic filler (F) is contained in an amount of 2 to 20 parts by mass per 100 parts by mass of the polymerizable monomer component (A);
(2) The acidic group-containing polymerizable monomer in the polymerizable monomer component (A) is a polymerizable monomer containing a phosphoric acid group;
(3) The polyvalent metal ion-eluting filler (B) shows the polyvalent metal ion elution amount of 5.0 to 500 meq/g—filler when 0.1 g of the filler is added to 10 ml of an aqueous solution containing 10% by weight of a maleic acid and is held at 23° C. for 24 hours; and
(4) The polyvalent metal ion-eluting filler has an average particle size of 0.01 to 5 μm.

Further, if the one-package dental adhesive composition of the present invention is used, for example, as the pre-treating material, the polymerizable monomer component containing the acidic group-containing polymerizable monomer is cured by polymerization at the time when the polymerizable composition such as the dental adhesive or the dental restorative (composite resin) applied thereon undergoes the curing reaction. In addition to the curing reaction, there also occurs ionic crosslinking of a polymer chain due to the action of the acidic group stemming from the acidic group-containing polymerizable monomer, water and polyvalent metal ion-eluting filler. Due to the synergistic effect of the curing by polymerization and the ionic crosslinking, therefore, a strong adhesive force is attained to both the enamel and the dentin, making it possible to firmly adhere and fix the composite resin or the bracket for correcting irregular teeth to the teeth.

Further, the greatest feature of the present invention is that the one-package dental adhesive composition is so adjusted that the polyvalent metal ions are eluted out in a predetermined amount from the polyvalent metal ion-eluting filler and, at the same time, the eluted polyvalent metal ions are adjusted to lie in a suitable range of concentration by using the volatile water-soluble organic solvent (diluting solvent). This suppresses the degree of gelling due to ionic bonding to a level free of problem during the preservation, and the one-package dental adhesive composition can be preserved in the form of one package. Besides, since the eluted polyvalent metal ions are diluted by using the volatile water-soluble organic solvent, the composition at the time of use is applied to the tooth surface and, thereafter, the air is blown thereto. Therefore, the water-soluble organic solvent can be easily volatilized and the composition can be enriched in a short period of time to attain a strong ionic bond based on the polyvalent metal ions. The synergistic effect due to the subsequent adhesion by radical polymerization and the adhesion by ionic crosslinking of the polymerized acidic group-containing polymerizable monomer is not almost impaired but is fully exhibited to maintain a large adhesive strength to both the enamel and the dentin.

BEST MODE FOR CARRYING OUT THE INVENTION

The one-package dental adhesive composition of the invention comprises (A) a polymerizable monomer component, (B) a polyvalent metal ion-eluting filler, (C) a volatile water-soluble organic solvent, and (D) water, and is used as a teeth pre-treating material that can be preserved in the form of one package. The one-package dental adhesive composition may be, further, blended with (E) a photopolymerization initiator, and can be used as a dental adhesive for adhering and fixing a composite resin or a bracket for correcting irregular teeth to the teeth. In either use, it is allowed to add various blending agents that have been known in the field of dentistry.
<Polymerizable Monomer Component (A)>

In this invention, the polymerizable monomer component (A) (hereinafter simply called "monomer component") is a component for imparting adhering property to various materials applied onto the adhesive composition, for example, to a dental adhesive used for adhering and fixing the bracket for correcting irregular teeth and the composite resin, or for imparting adhering property to the composite resin. In order to obtain an etching capability to the teeth, it is necessary that at least not less than 5% by mass of the polymerizable monomer component (A) is an acidic group-containing polymer (A1). If the amount of the acidic group-containing polymer (A1) is small, the adhesive composition fails to exhibit the etching capability to the teeth to a sufficient degree and it becomes necessary to pre-treat the teeth to attain a sufficient degree of adhesive strength to the teeth.

The monomer component (A) may all be the acidic group-containing polymer (A1). To adjust the strength of the junction interface and the permeability of the pre-treating material into the teeth, and to obtain further excellent adhesive strength to the teeth and durability of adhesion, however, it is desired that a polymerizable monomer (A2) without acidic group is further contained.

When the adhesive composition of the invention is used as a teeth pre-treating material, for example, it is desired that the content of the acidic group-containing polymer (A1) in the monomer component (A) is in a range of 5 to 80% by mass and, particularly, 20 to 70% by mass. When the adhesive composition is used as a dental adhesive, it is desired that the content of the acid group-containing polymer (A1) in the monomer component (A) is 5 to 50% by mass and, particularly, 10 to 30% by mass. In either case, the residue is a polymerizable monomer (A2) without acidic group, and if the amount of the acidic group-containing polymerizable monomer (A1) is small, the adhesive strength to the enamel tends to decrease. If the amount thereof is large, on the other hand, the adhesive strength to the dentin tends to decrease. Here, when used as the dental adhesive, the adhesive composition contains the polymerizable monomer (A2) without acidic group in an amount larger than that of when it is used as the teeth pre-treating material, in order to impart sufficient degree of adhering property to the composite resin or to the bracket for correcting irregular teeth.

Acidic Group-Containing Polymerizable Monomer (A1):

As the acid group-containing polymerizable monomer (A1) in this invention, a known compound can be used without any particular limitation provided it has at least one acidic group and at least one polymerizable unsaturated group in a molecule thereof.

Described below are examples of the acidic group possessed in the molecules of the monomer (A1).

Examples of the Acidic Group:

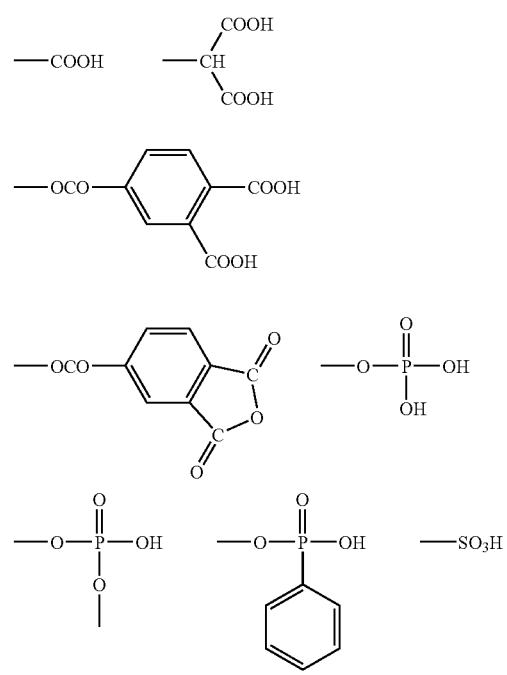

As the polymerizable unsaturated group possessed in the molecules of the monomer (A1), there can be exemplified acryloyl group, methacryloyl group, acrylamide group, methacrylamide group, vinyl group, allyl group, ethenyl group and styryl group.

In the present invention, compounds expressed by the following formulas are representative concrete examples of the polymerizable monomer (A1) having the above acidic group and the polymerizable unsaturated group in the molecules thereof used.

Representative Examples of the Acidic Group-Containing Polymer (A1):
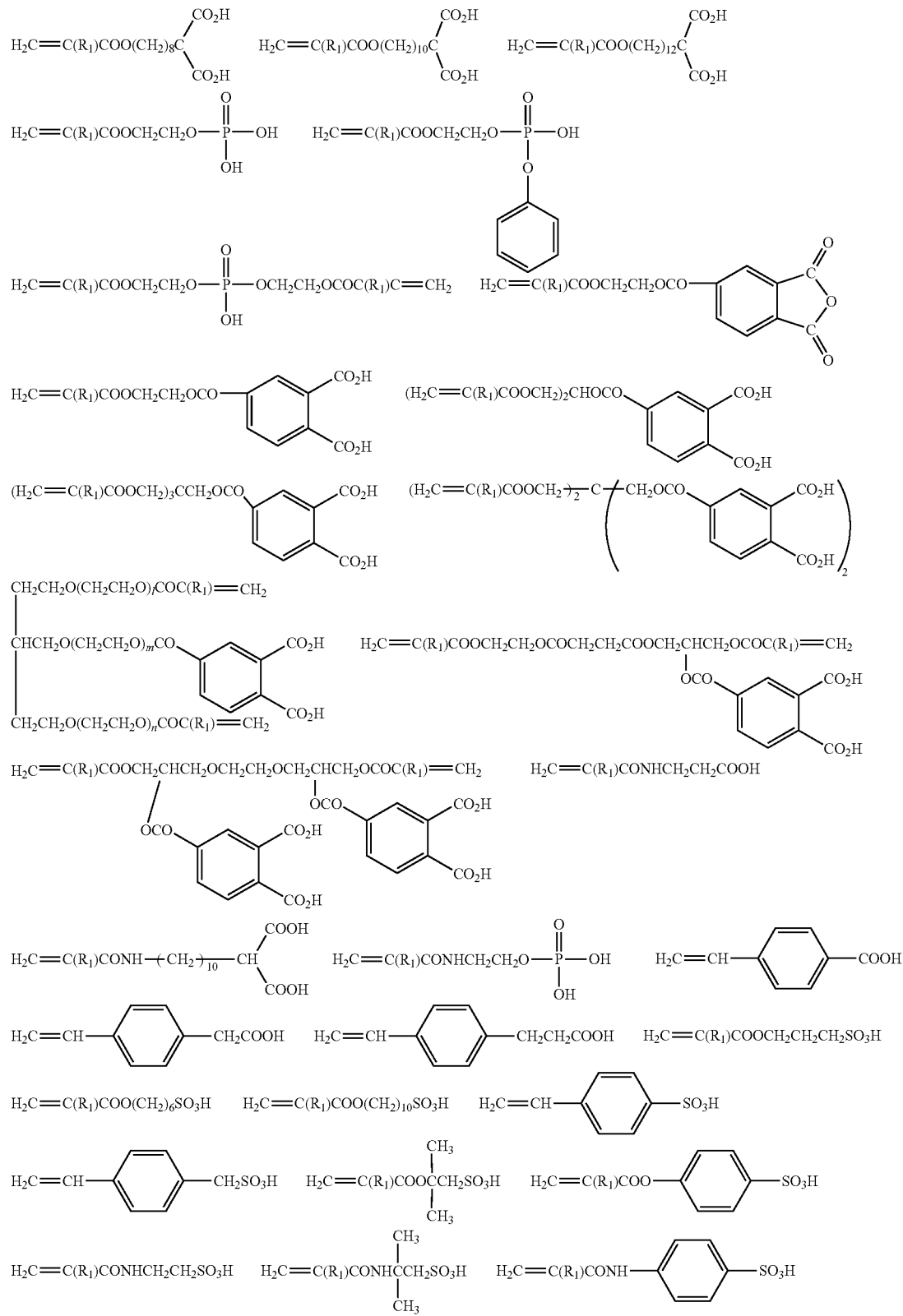
$l + m + n = 3.5$ wherein $R^1$ is a hydrogen atom or a methyl group.

In addition to the above compounds, there can be used vinyl phosphonates in which a phosphonic acid group is directly bonded to a vinyl group, as well as acrylic acid, methacrylic acid and vinyl sulfonate as the acidic group-containing polymers (A1).

The acidic group-containing polymers (A1) exemplified above can be used alone or being mixed together in two or more kinds. Among them, it is desired to use a compound (polybasic acid compound) in which the acid in the molecules thereof has a valency of not smaller than 2 from the standpoint of enhancing the ionic bonding to the polyvalent metal ions released from the polyvalent metal ion-eluting filler (B) that will be described later and of obtaining a large adhesive strength. The polybasic acid compound may have two or more monovalent acid groups in the molecules or may have at least one acid group having a valency of not less than 2 in the molecules thereof. Use of the polybasic acid compound only as the basic group-containing polymerizable monomer (A1) is desirable from the standpoint of improving the strength decreasing, however, the preservation stability in the form of one liquid to some extent. It is, therefore, more desired to use the polybasic acid compound and the acidic compound in which the acid in the molecules thereof has a valency of 1 in combination from the standpoint of attaining both adhesive strength and preservation stability.

Further, when the above polybasic acid compound and a monovalent acidic compound are used in combination as the acidic group-containing polymerizable monomer (A1), it is most desired that either compound contains an acid group of the phosphoric acid type (e.g., $-O-P(=O)(OH)_2$, $(-O-)_2 P(=O)OH$, etc.) as the acidic group. The system which uses the acidic group-containing polymerizable monomers (A1) in the above combination exhibits not only a high action for teeth-deliming (presumably due chiefly to the acid group of the phosphoric acid type having a strong acidity) but also a substantially large bonding force to the teeth, making it possible to obtain a particularly large adhesive strength and to obtain favorable preservation stability in the form of one solution.

From the standpoint of curing rate, further, it is desired that the acidic group-containing polymerizable monomer (A1) is a compound having acryloyl group, methacryloyl group, acrylamide group or methacrylamide group as the polymerizable unsaturated group.

Polymerizable Monomer (A2) without Acidic Group:

As the polymerizable monomer (A2) without acidic group that can be used in combination with the monomer (A1), a known compound can be used without any particular limitation provided it satisfies the conditions of containing no acidic group and having at least one polymerizable unsaturated group. As the polymerizable unsaturated group possessed by the polymerizable monomer, there can be exemplified those which are the same as those exemplified above concerning the monomer (A1) and, particularly desirably, acryloyl group, methacryloyl group, acrylamide group and methacrylamide group.

The following (meth)acrylate monomers are representative examples of the polymerizable monomer (A2) and can be used alone or in a combination of two or more kinds.

1. Mono(meth)acrylate Monomers:
methyl(meth)acrylate,
ethyl(meth)acrylate,
glycidyl(meth)acrylate,
2-cyanomethyl(meth)acrylate,
benzyl(meth)acrylate,
polyethylene glycol mono(meth)acrylate,
allyl(meth)acrylate,
2-hydroxyethyl(meth)acrylate,
glycidyl(meth)acrylate,
3-hydroxypropyl(meth)acrylate,
glyceryl mono(meth)acrylate, and
2-(meth)acryloxyethylacetyl acetate.

2. Polyfunctional (meth)acrylate Monomers:
ethylene glycol di(meth)acrylate,
diethylene glycol di(meth)acrylate,
triethylene glycol di(meth)acrylate,
nonaethylene glycol di(meth)acrylate,
propylene glycol di(meth)acrylate,
dipropylene glycol di(meth)acrylate,
2,2'-bis[4-(meth)acryloyloxyethoxyphenyl]propane,
2,2'-bis[4-(meth)acryloyloxyethoxyethoxyphenyl]propane,
2,2'-bis{4-[3-(meth)acryloyloxy-2-hydroxypropoxy]phenyl}propane,
1,4-butanediol di(meth)acrylate,
1,6-hexanediol di(meth)acrylate,
trimethylolpropane tri(meth)acrylate,
urethane(meth)acrylate, and
epoxy(meth)acrylate.

It is also allowable to use polymerizable monomers other than the above (meth)acrylate monomers being mixed together. As the other polymerizable monomers, there can be exemplified fumaric ester compounds such as monomethyl fumarate, diethyl fumarate and diphenyl fumarate; styrene compounds such as styrene, divinylbenzene, α-methylstyrene and α-methylstyrene dimer; and allyl compounds such as diallyl phthalate, diallyl terephthalate, diallyl carbonate and allyl diglycol carbonate. These other polymerizable monomers can be used alone or being mixed together in two or more kinds.

In the present invention, further, when a highly hydrophobic polymerizable monomer is used as the polymerizable monomer (A2), it is desired to use an amphipatic monomer such as 2-hydroxyethyl(meth)acrylate or 2-hydroxypropyl (meth)acrylate in combination. Use of the amphipatic monomer makes it possible to prevent the isolation of water which is an essential component of the adhesive composition of the invention, to maintain homogeneity of the composition and to obtain a stable and large adhesive strength.

<Polyvalent Metal Ion-Eluting Filler (B)>

The polyvalent metal ion-eluting filler (hereinafter simply called polyvalent metal filler) used in the present invention has a function of the filler for improving the mechanical strength of the adhesive layer and a function of eluting out polyvalent metal ions for ionic crosslinking with the polymer of the acidic group-containing polymerizable monomer. As described already, the present invention maintains a large adhesive strength owing to the synergistic effect of the curing by polymerization and the ionic crosslinking. In order to form the ionic crosslinking, a polyvalent metal filler is used as the component (B).

In the present invention, it is important that the amount of the polyvalent metal ions eluted out from the polyvalent metal filler (B) into the adhesive composition is adjusted to be 1.0 to 7.0 meq per gram of the monomer component (A). Upon adjusting the amount of the polyvalent metal ions eluted per gram of the monomer component (A) to lie in the above range, a strong adhesive layer can be formed in the interface to the teeth relying upon a suitable degree of ionic crosslinking. If the eluted amount of the polyvalent metal ions is smaller than the above range, the ionic crosslinking becomes insufficient and the adhesive strength to the teeth decreases. If the eluted amount exceeds the above range, the capability of the acidic group-containing polymer (A1) to delime the teeth decreases and, besides, causing an increase in the amount of the volatile water-soluble organic solvent (C) which is necessary for maintaining the preservation stability in the form of one package. When the adhesive composition is applied to the surfaces of the teeth and the air is blown, therefore, the adhesive component tends to be present in insufficient amounts in the interface to the teeth. In either case, therefore, the adhesive strength tends to decrease.

Here, the polyvalent metal ions are the metal ions having a valency of two or more and are capable of being bonded to the acidic group possessed by the polymerizable monomer (A1), and can be represented by calcium, strontium, barium, aluminum, zinc or lanthanoid. From the standpoint of adhesive strength, in particular, it is desired to contain trivalent ions such as of aluminum or the like.

The polyvalent metal filler (B) may contain monovalent metal ions such as of sodium so far as it is capable of eluting out the polyvalent metal ions within the above range. However, the monovalent metal ions that are contained in too large amounts affect the ionic crosslinking which is based upon the polyvalent metal ions. It is, therefore, desired that the content of the monovalent metal ions is as small as possible. Usually, it is desired that the content of the monovalent metal ions is less than 10 mol % and, particularly, less than 5 mol % of the content of the polyvalent metal ions.

In the present invention, the amount (meq) of the polyvalent metal ions eluted out from the polyvalent metal filler (B) into the adhesive composition is the one obtained by converting the amount of ionic bond with the monomer component (A) by the eluted polyvalent metal ions into a milliequivalent per gram of the monomer component (A), and represents the sum of values obtained by multiplying the respective polyvalent metal ion concentrations (mmol/g) per gram of the monomer component (A) by the valencies of the respective metal ions. Further, the ion concentrations can be measured by the ICP emission spectroscopy or the atomic absorption spectroscopy.

After the adhesive composition has been prepared, further, the polyvalent metal ions are all eluted out from the polyvalent metal filler (B) over 3 hours to 12 hours at room temperature (23° C.). Therefore, the above amount of the polyvalent metal ions is substantially equal to the amount of the polyvalent metal ions at room temperature (23° C.) 24 hours after the preparation, and can be calculated from the total amount of the polyvalent metal ions contained in the polyvalent metal filler (B) and from the amount of the monomer component (A) in the adhesive composition.

There is no particular limitation on the polyvalent metal filler (B) used in the present invention provided it is capable of eluting out polyvalent metal ions in an amount within the above-mentioned range. When the polyvalent metal ions are contained as a salt of counter anions that may eluted out simultaneously with the polyvalent metal ions, the counter anions that are eluted/dissociated may adversely affect the adhesive strength. In the present invention, therefore, it is desired to use the polyvalent metal filler (B) which does not permit the counter ions to elute out simultaneously with the polyvalent metal ions. As the polyvalent metal filler satisfying the above conditions, glasses can be exemplified having skeletons of a chain-like, layer-like or mesh-like structure and containing polyvalent metal ions in the gaps of the skeletons.

As the glasses, there can be preferably used those having an oxide glass component, such as aluminosilicate glass, borosilicate glass or soda ash glass, and those having a fluoride glass component, such as zirconium fluoride glass. After having eluted out the polyvalent metal ions, the polyvalent metal filler (B) comprising glasses containing these components turns into porous particles having a mesh-like structure and works to improve the strength of the cured body of the adhesive composition.

The present invention more preferably uses the polyvalent metal filler (B) comprising the aluminosilicate glass from the standpoint of improving the strength of the cured body and, most preferably, uses the polyvalent metal filler (B) comprising the fluoroaluminosilicate glass having a so-called gradually fluorine-releasing property gradually releasing fluoride ions for reinforcing the dentin after having been adhered.

The polyvalent metal ion elution property of the polyvalent metal filler (B) can be controlled by varying the ratio of blending various elements contained in the filler. For example, if the contents of polyvalent metal ions such as of aluminum, calcium, etc. are increased, the amounts of their elution, usually, increase. The amount of elution of polyvalent metal ions can be, further, varied by changing the contents of sodium and phosphorus. Therefore, the polyvalent metal ion elution property can be controlled relatively easily.

The elution property of the polyvalent metal filler (B) can be controlled by using a generally known method. A representative known method comprises treating the polyvalent metal filler (B) with an acid to remove the polyvalent metal ions in advance from the surfaces of the filler, and controlling the elution property. The acid used for this method is a generally known inorganic acid, such as hydrochloric acid or nitric acid, or organic acid, such as maleic acid or citric acid. The concentration of acid and the treating time may be suitably determined depending upon the amount of ions that are to be removed.

Further, the fluoroaluminosilicate glass that is preferably used in the invention as the polyvalent metal filler (B) is a widely known one that is used for the dental cement such as glass ionomer cement. The widely known fluoroaluminosilicate glass has the following composition as expressed by ionic mass %.

Silicon: 10 to 33%, particularly, 15 to 25%
Aluminum: 4 to 30%, particularly, 7 to 20%
Alkaline earth metals: 5 to 36%, particularly, 8 to 28%
Alkali metal: 0 to 10%, particularly, 0 to 10%
Phosphorus: 0.2 to 16%, particularly, 0.5 to 8%
Fluorine: 2 to 40%, particularly, 4 to 40%
Oxygen: remainder There can be further favorably used those in which part or whole of calcium in the alkaline earth metals is substituted by magnesium, strontium or barium. Most generally, further, the above alkali metal is sodium, and there can be favorably used even those in which part or whole of sodium is substituted by lithium or potassium. As required, further, the glass in which part of aluminum is substituted by titanium, yttrium, zirconium, hafnium, tantalum or lanthanum can be used as the polyvalent metal filler (B).

There is no particular limitation on the shape of particles of the polyvalent metal filler (B) used in the invention, and the particles may be of a shape as pulverized through an ordinary pulverization or may be of a spherical shape. As required, the plate-like or fibrous particles may also be mixed together.

From the standpoint of easily producing the adhesive composition in which the filler is homogeneously dispersed, further, it is desired that the polyvalent metal filler (B) has an average particle size ($D_{50}$) in a range of 0.01 μm to 5 μm, particularly, 0.05 μm to 3 μm and, most desirably, 0.1 μm to 2 μm in terms of volume as measured by, for example, the laser diffraction scattering method. From the standpoint of easily adjusting the amount of elution of polyvalent metal ions to lie in the above-mentioned range, further, it is desired that when 0.1 g of the filler is immersed in 10 ml of an aqueous solution containing 10% by weight of maleic acid at a temperature of 23° C. for 24 hours, the eluted amount of the polyvalent metal ions is 5.0 to 500 meq/g—filler and, particularly, 10 to 100 meq/g—filler. The amount of the polyvalent metal ions at this moment, too, can be measured by the ICP emission spectroscopy or by the atomic absorption spectroscopy. The amount of the polyvalent metal ions eluted out after the passage of 24 hours under the above conditions will hereinafter be also called "24 hour-eluted ion amount".

<Water-Soluble Organic Solvent (C)>

The present invention uses a volatile water-soluble organic solvent (C) in order to prevent the gelling stemming from the polyvalent metal ions eluted from the polyvalent metal filler (B) used in an amount described above and to improve the preservation stability. That is, upon diluting the eluted polyvalent metal ions into a particular concentration by using the water-soluble organic solvent (C), the composition can be preserved in the form of one liquid (i.e., in the form of one package) in which all components are blended together.

The water-soluble organic solvent (C) is blended in an amount in a range of 30 to 150 parts by mass per 100 parts by mass of the monomer component (A) satisfying a condition expressed by the following formula (I):

$$\alpha \geq 20 \cdot X \quad (I)$$

wherein α is the amount of the water-soluble organic solvent (C) blended per 100 parts by mass of the polymerizable monomer component (A), X is a number representing the amount of the polyvalent metal ions eluted out from the polyvalent metal ion-eluting filler (B) or the amount (meq) per gram of the polymerizable monomer component (A).

That is, if the water-soluble organic solvent (C) is blended in an amount of less than 30 parts by mass, the adhesive composition permeates little into the teeth and a sufficiently large adhesive force is not obtained. If the blending amount thereof exceeds 150 parts by mass, the organic solvent remains on the surface of the teeth unless the air is blown to an excess degree. Therefore, the adhesive force is not obtained to a sufficient degree and, besides, the adhesive component concentration tends to become lean. After the air is blown, therefore, the adhesive component is present in decreased amounts in the layer remaining on the surface of the teeth, and the adhesive force decreases.

Even when the amount of the water-soluble organic solvent (C) that is blended is in the range of 30 to 150 parts by mass, the polyvalent metal ions are diluted to a low degree if the condition of the formula (I) is not satisfied (i.e., if α<20·X), gelling takes place. As a result, it becomes difficult to preserve the adhesive composition in the form of one package blending all components together.

From the standpoint of obtaining a large strength of adhesion to the dentin in the present invention, it is desired that the water-soluble organic solvent (C) is blended in an amount in a range of 60 to 100 parts by mass. From the standpoint of improving the preservation stability, further, it is desired that the above blending amount satisfies the following formula (II):

$$\alpha \geq 25 \cdot X \quad (II)$$

wherein α and X are as defined in the formula (I) above.

Further, even when the adhesive composition of the invention is used as either a material for pre-treating the teeth or a dental adhesive, the composition is applied onto the surface of the tooth and, thereafter, the air is blown to volatilize the water-soluble organic solvent (C). That is, upon volatilizing the water-soluble organic solvent (C), the effective component is concentrated on the tooth surface, the ionic crosslinking is accelerated between the acidic group-containing polymerizable monomer and the polyvalent metal ions, and excellent strength of adhesion is obtained to the surfaces of dentin. Therefore, the water-soluble organic solvent (C) used in the present invention must be soluble in water and must, at the same time, be volatile at room temperature.

In this specification, "volatile" stands for that the boiling point under 760 mmHg is not higher than 100° C. and the vapor pressure at 2° C. is not lower than 1.0 KPa. Further, "water-soluble" stands for that the solubility in water at 20° C. is not smaller than 20 g/100 ml.

As the volatile water-soluble organic solvent, there can be exemplified methanol, ethanol, n-propanol, isopropyl alcohol, acetone, methyl ethyl ketone and the like. As required, these organic solvents can be used in a plural kinds being mixed together. By taking toxicity to living body into consideration, it is desired to use ethanol, isopropyl alcohol and acetone.

<Water (D)>

In the present invention, water which is the component (D) serves as a solvent for homogeneously dispersing various components, and is necessary for teeth-deliming and for accelerating the ionic bond between the acidic group-containing polymerizable monomer (A1) and the polyvalent metal filler (B). As the water, there is preferably used distilled water or deionized water without substantially containing impurities detrimental to the storage stability and medicinal components.

Water which is the component (D) is added in an amount of 3 to 30 parts by mass and, particularly, 5 to 25 parts by mass per 100 parts by mass of the monomer component (A). If the amount of water that is added is smaller than the above range, the teeth are not delimed or the ionic crosslinking is not effected to a sufficient degree, and a large adhesive strength is not obtained. If water is used in an amount larger than the above range, on the other hand, the water is less removed by the blow of the air after the adhesive composition is applied to the tooth surface; i.e., much water remains on the tooth surface, and a sufficiently large adhesive force is not obtained.

<Photopolymerization Initiator (E)>

As described already, the adhesive composition of the present invention can be used as a material for pre-treating the teeth or a dental adhesive. When used as the dental adhesive, a photopolymerization initiator (E) must be added to cure the adhesive composition itself.

As the photopolymerization initiator (E), there can be used a compound that forms radical species upon being irradiated with light or a mixture thereof with a polymerization accelerator.

Described below are examples of the compound which undergoes the decomposition upon being irradiated with light and forms radical species capable of undergoing the polymerization.

α-Diketone:
camphor quinone, benzyl, α-naphthyl, acetonaphthene, naphthoquinone, 1,4-phenanthrenequinone, 3,4-phenanthrenequinone and 9,10-phenanthrenequinone.

Thioxanthone:
2,4-diethylthioxanthone, etc.

α-Aminoacetophenone:
2-benzyl-dimethylamino-1-(4-morpholinophenyl)-butanone-1,
2-benzyl-diethylamino-1-(4-morpholinophenyl)-butanone-1,
2-benzyl-dimethylamino-1-(4-morpholinophenyl)-propanone-1, 2-benzyl-diethylamino-1-(4-morpholinophenyl)-propanone-1,
2-benzyl-dimethylamino-1-(4-morpholinophenyl)-pentanone-1,
2-benzyl-diethylamino-1-(4-morpholinophenyl)-pentanone-1.

Acylphosphinoxide Derivatives:
2,4,6-trimethylbenzoyldiphenylphosphinoxide, and bis(2,6-dimethoxybenzoyl)-2,4,4-trimethylpentylphosphinoxide.

As the above-mentioned polymerization accelerator, there can be used tertiary amines, barbituric acids and mercapto compounds. Their concrete examples are as described below.

Tertiary Amine:
N,N-dimethylaniline,
N,N-diethylaniline,
N,N-di-n-butylaniline,
N,N-dibenzylaniline,
N,N-dimethyl-p-toluidine,
N,N-diethyl-p-toluidine,
N,N-dimethyl-m-toluidine,
p-bromo-N,N-dimethylaniline,
m-chloro-N,N-dimethylaniline,
p-dimethylaminobenzaldehyde,
p-dimethylaminoacetophenone,
p-dimethylaminobenzoic acid,
p-dimethylaminobenzoic ethyl ester,
p-dimethylaminobenzoic amyl ester,
N,N-dimethylanthranic acid methyl ester,
N,N-dihydroxyethylaniline,
N,N-dihydroxyethyl-p-toluidine,
p-dimethylaminophenetyl alcohol,
p-dimethylaminostylbene,
N,N-dimethyl-3,5-xylidene,
4-dimethylaminopyridine,
N,N-dimethyl-α-naphthylamine,
N,N-dimethyl-β-naphthylamine,
tributylamine,
tripropylamine,
triethylamine,
N-methyldiethanolamine,
N-ethyldiethanolamine,
N,N-dimethylhexylamine,
N,N-dimethyldodecylamine,
N,N-dimethylstearylamine,
N,N-dimethylaminoethyl acrylate,
N,N-dimethylaminoethyl methacrylate and
2,2'-(n-butylimino)diethanol.

Barbituric Acid:
5-butylbarbituric acid, and
1-benzyl-5-phenylbarbituric acid.

Mercapto Compounds:
dodecylmercaptane, and
pentaerythritol tetrakis(thioglycolate).

There is no particular limitation on the amount of blending the photopolymerization initiator (E) provided the amount is enough for curing the adhesive composition, and the amount may be suitably selected. Generally, however, the amount of the photopolymerization initiator (E) is in a range of 0.01 to 10 parts by mass and, particularly, 0.1 to 5 parts by mass per 100 parts by mass of the monomer component (A). If the amount is smaller than 0.01 part by mass, the polymerization becomes insufficient. If the amount exceeds 10 parts by mass, on the other hand, the strength of the formed polymer decreases, which is not desirable.

<Inorganic Filler (F)>

An inorganic filler (F) can be added to the adhesive composition of the invention in order to increase the strength of the pre-treating layer or the adhesive layer after cured. The inorganic filler (F) does not elute out polyvalent metal ions, and can be distinguished from the above-mentioned polyvalent metal filler (B). As the inorganic filler (F), a composite inorganic oxide can be preferably used, such as silica, silica-zirconia, silica-titania or silica-alumina.

Though there is no particular limitation, the inorganic filler (F) has a primary particle size of desirably not larger than 5 μm, more desirably, 0.001 to 1 μm and, most desirably, 0.01 to 0.5 μm. There is no limitation, either, on the shape of the particles; i.e., the particles may assume an amorphous shape or a spherical shape.

The inorganic filler (F) is treated with a surface-treating agent as represented by a silane coupling agent to be hydrophobic in order to improve affinity to the polymerizable monomer component (A) and to further improve the mechanical strength and the resistance against water.

As the silane coupling agent for imparting hydrophobic property, there can be preferably used:
methyltrimethoxysilane, methyltriethoxysilane,
methyltrichlorosilane, dimethyldichlorosilane,
trimethylchlorosilane, vinyltrimethoxysilane,
vinyltriethoxysilane, vinyltrichlorosilane,
vinyltriacetoxysilane,
vinyltris (β-methoxyethoxy) silane,
γ-methacryloyloxypropyltrimethoxysilane,
γ-methacryloyloxypropyltris (β-methoxyethoxy) silane,
γ-chloropropyltrimethoxysilane,
γ-chloropropylmethyldimethoxysilane,
γ-glycidoxypropyltimethoxysilane,
γ-glycidoxypropylmethyldiethoxysilane,
β-(3,4-epoxycyclohexyl)ethyltrimethoxysilane,
N-phenyl-γ-aminopropyltrimethoxysilane, and
hexamethyldisilazane.

The inorganic filler (F) is added preferably in an amount in a range of 2 to 20 parts by mass and, particularly, 5 to 10 parts by mass per 100 parts by mass of the monomer component (A). If the amount is smaller than this range, the effect for improving the strength is not obtained to a sufficient degree. If used in an amount larger than the above range, the viscosity increases, permeability to the dentin is impaired, and the effect for improving the strength of adhesion to the teeth is not obtained to a sufficient degree.

<Other Blending Agents>

The one-package dental adhesive composition of the present invention may be blended with an organic viscosity-imparting agent of a high molecular compound such as polyvinyl pyrrolidone, carboxymethyl cellulose or polyvinyl alcohol. Further, various additives such as ultraviolet ray absorber, dye, antistatic agent, pigment, perfume and the like may be selectively used as required.

Further, when used as the pre-treating material, the adhesive composition of the invention that is applied to the surfaces of the teeth maintains the applied surfaces covered with the adhesive and with the composite resin. Therefore, the applied surfaces are not almost affected by oxygen in the air at the time of curing, and the adhesive force is not affected by oxygen in the air. In order to minimize hampering to the curing by oxygen dissolved in the composition, however, the above-mentioned tertiary amine may be added.

<Adhesive Composition>

The one-package dental adhesive composition of the present invention is effectively suppressed from being gelled by the elution of polyvalent metal ions, and exhibits excellent preservation stability enabling the above-mentioned components to be mixed together in predetermined amounts. Therefore, the dental adhesive composition of the invention can be used while being preserved in the form of one package. That is, the one-package dental adhesive composition can be used without requiring a cumbersome operation of mixing various components together, contributing to decreasing laborious work by the dentists, and maintains a predetermined adhesive strength with stability. The above various components may be mixed together according to a known method employed for the materials for pre-treating the teeth and the dental adhesives. Generally, components to be blended are all weighed under inert light such as red light, and are mixed together until a homogeneous solution is obtained.

Of the adhesive compositions of the invention thus obtained, the one of the type which is not blended with the photopolymerization initiator (E) can be used as a material for pre-treating the teeth to improve the force of adhering the object that is to be adhered to the teeth in the field of dental treatment. When the adhesive composition of the invention is used as the pre-treating material, two steps of pre-treatment, i.e., etching the dentin and accelerating the permeation to the teeth, can be executed in one step only by using the pre-treating material.

That is, the adhesive composition of the invention can be used as a self-etching primer composition for adhering the composite resin, bracket or prosthetic material to the teeth. For example, the adhesive composition may be applied to the teeth prior to applying the adhesive for composite resin, prior to applying the adhesive for bracket or prior to applying the adhesive for prosthetic material. Here, the adhesive for composite resin, the adhesive for bracket or the adhesive for prosthetic material may be the one of the chemically polymerizing type. Among them, however, it is desired that the adhesive for composite resin and the adhesive for bracket are those of the photocurable type blended with a photopolymerization initiator from the standpoint of simplicity in operation. As the photocurable adhesive for composite resin or for bracket, widely known adhesives can be used without any limitation. As the adhesive for composite resin, for example, there can be used those disclosed in JP-A-6-9327, JP-A-6-24928 and JP-A-8-319209. As the adhesive for bracket, further, there can be used those disclosed in, for example, JP-T-2005-529637, JP-T-2004-510796 and JP-A-5-85912. Or, the composite resin that will be described later may be used as an adhesive for bracket.

Further, the adhesive composition of the invention used as the pre-treating material can also be favorably used for the restored portion of the teeth prior to filling the composite resin that is used without applying the dental adhesive. This mode of use is desirable owing to its particularly excellent operability when the composite resin is of the photocurable type. Concretely, the pre-treating material is applied onto the tooth surface to stay thereon without cured with light. Thereafter, the photocurable composite resin is applied on the applied surface and is cured with light. Therefore, not only the photocurable composite resin but also the underlying pre-treating material are simultaneously cured with light. In contrast with irradiating light twice for curing the pre-treating material and for curing the photocurable composite resin, therefore, the photocurable composite resin can be adhered to the dentin by irradiating light one time, which is a great improvement in the operability. The photocurable composite resins used for this embodiment have been disclosed in, for example, JP-A-2005-089729, JP-A-2001-139411, JP-A-2000-026226, JP-A-10-114616 and JP-A-06-157230.

Further, upon being blended with the above photopolymerization initiator (E), the adhesive composition of the present invention can also be used as a dental adhesive for adhering and fixing the composite resin or the bracket for correcting irregular teeth. When used as such an adhesive, the dentin is pre-treated with the adhesive itself. Therefore, there is no need of using the pre-treating material contributing to further decreasing the laborious work by dentists. Besides, a predetermined adhesive strength can be stably maintained without dispersion.

EXAMPLES

The invention will now be concretely described by way of Experimental Examples to which only, however, the invention is in no way limited.

Experimental Example (I) demonstrates the effect of when the adhesive composition of the invention is used as a material for pre-treating the teeth, and Experimental Example (II) demonstrates the effect of when the adhesive composition of the invention is used as a dental adhesive.

Abbreviated names, abbreviated symbols, method of measuring the adhesive strength, method of evaluating the preservation stability and method of measuring the amounts of polyvalent metal ions appearing in Experiments are as described below.

Polymerizable Monomer Components (A)

[Acidic Group-Containing Polymerizable Monomers (A1)]

PM: A mixture of 2-methacryloyloxyethyldihydrogen phosphate and bis(2-methacryloyloxyethyl)hydrogen phosphate at a ratio of 2:1.

MDP: 10-Methacryloyloxydecyldihydrogen phosphate.

MAC-10: 11-Methacryloyloxy-1,1-undecanedicarboxylic acid.

4-META: 4-Methacryloyloxyethyltrimellitic acid.

[Polymerizable Monomers (A2) Without Acidic Group]

D26E: 2,2'-Bis(4-(methacryloxyethoxy)phenyl)propane.

BisGMA: 2,2'-Bis[4-(2-hydroxy-3-methacryloxypropoxy)phenyl]propane.

3G: Triethylene glycol dimethacrylate.

HEMA: 2-Hydroxyethyl methacrylate.

MMA: Methyl methacrylate.

AAEM: 2-Methacryloxyethylacetyl acetate.

Polyvalent Metal Fillers (B)

MF1: Polyvalent metal filler obtained in Preparation Example 1 (average particle size: 0.5 μm, amount of ions eluted out in 24 hours: 10 meq/g—filler).

MF2: Polyvalent metal filler obtained in Preparation Example 2 (average particle size: 0.5 μm, amount of ions eluted out in 24 hours: 25 meq/g—filler).

MF3: Polyvalent metal filler obtained in Preparation Example 3 (average particle size: 0.5 μm, amount of ions eluted out in 24 hours: 50 meq/g—filler).

Volatile Water-Soluble Organic Solvents (C)

Et-OH: Ethyl alcohol.

IPA: Isopropyl alcohol.

Acetone

Polymerization Initiator (E)

CQ: Camphor quinone.

DMBE: Ethyl p-N,N-dimethylaminobenzoate.

DMPT: N,N-Dimethyl-p-toluidine.

MDEOA: Methyldiethanolamine.

TPO: 2,4,6-Trimethylbenzoyldiphenylphosphinoxide.

BDTPO: Bis(2,6-dimethoxybenzoyl)-2,4,6-trimethylphenylphosphinoxide.

TAZ: 2,4,6-Tris(trichloromethyl)-S-triazine.

IMDPI: 4-Methylphenyl-4'-isopropylphenyliodonium tetrakis(pentafluorophenyl)borate.

Polymerization Inhibitors
HQME: Hydroquinonemonomethyl ether.
BHT: 2,6-Di-t-butyl-p-cresol.
Inorganic Fillers (F)
Si—Ti: Spherical silica-titania of a particle size of 0.08 μm (treated with γ-methacryloyloxypropyltrimethoxysilane to be hydrophobic).
F1: Amorphous silica of a particle size of 0.02 μm (treated with methyltrichlorosilane).
F2: A mixture of a spherical silica-zirconia of a particle size of 0.4 μm (treated with γ-methacryloyloxypropyl trimethoxysilane to be hydrophobic) and a spherical silica-titania of a particle size of 0.08 μm (treated with γ-methacryloyloxypropyltrimethoxysilane to be hydrophobic) at a mass ratio of 70:30.
F3: A mixture of a pulverized quartz of a particle size of 6 μm (treated with γ-methacryloyloxypropyl trimethoxysilane to be hydrophobic) and the amorphous silica (F1) at a mass ratio of 70:30.

Method of Measuring the Strength of Adhering the Composite Resin

Bovine foreteeth were pulled out within 24 hours after butchered and were ground with an emery paper of #600 while pouring water until the flat enamel surfaces were reached to be in parallel with the labial faces in order to prepare teeth for testing the strength of adhesion to the enamel. Similarly, further, the teeth were ground until the flat dentin surfaces were reached to prepare teeth for testing the strength of adhesion to the dentin.

Next, the compressed air was blown to the ground surfaces of each of the teeth for testing for about 10 seconds to dry, and a double-sided adhesive tape having a hole of a diameter of 3 mm was fixed to the flat surfaces. Next, a paraffin wax (0.5 mm thick) having a through hole of a diameter of 8 mm was fixed thereto so as to be in concentric with the above hole to thereby form a mimic cavity.

In the Experimental Example (I) for evaluating the material for pre-treating the teeth, the adhesive compositions (pre-treating materials) prepared in experiments were applied into the mimic cavities, left to stand for 20 seconds and, thereafter, the compressed air was blown for about 10 seconds to dry. Thereafter, a dental composite resin prepared in preparation example described later was applied thereon, and was irradiated with light by using a visible ray irradiator (Power Light manufactured by Tokuyama Dental Co.) for 30 seconds to prepare adhesion test pieces.

In the Experimental Example (II) for evaluating the adhesives, the adhesive compositions (adhesives) prepared in experiments were applied into the mimic cavities, left to stand for 20 seconds and, thereafter, the compressed air was blown for about 10 seconds to dry. Next, like the above, the adhesives were cured by being irradiated with light by using the visible ray irradiator for 10 seconds. Thereafter, a dental composite resin (Palfeek Estelight Σ, manufactured by Tokuyama Dental Co.) was applied thereon, and was irradiated with light by using the visible ray irradiator for 30 seconds to prepare adhesion test pieces.

After dipped in water at 37° C. for 24 hours, the adhesion test pieces were pulled by using a tension tester (Autograph, manufactured by Shimazu Mfg. Co.) at a crosshead speed of 2 mm/min. to measure the tensile adhesive strength between the dentin and the composite resin. Four test pieces were measured for their tensile adhesive strength by the above method per each testing, and an average value thereof was regarded to be the strength of adhesion to the enamel or to the dentin in order to evaluate the strength of adhering the composite resin.

Method of Measuring the Strength of Adhering the Bracket for Correcting Irregular Teeth Bovine foreteeth were pulled out within 24 hours after butchered and were polished on their labial faces with a tooth surface-polishing agent (manufactured by Neo Seiyaku Co.) followed by washing with tap water and blowing with the compressed air to dry.

Adhesive compositions (pre-treating materials) prepared in Experimental Example (I) were applied to the polished surfaces and, after left to stand for 20 seconds, the compressed air was blown thereto for about 10 seconds to dry. The base adhesion portion (area, 10.5 mm$^2$) of a metal bracket for correction (for middle cutting tooth, manufactured by Dents Ply Sankin Co.) to which the adhesive for correction has been applied was press-contacted to the surface on which the pre-treating material has been applied, and the excess of the adhesive that is swelling out was removed by using the end of a pair of tweezers. Thereafter, the central portion and the terminal end side of the bracket were irradiated with light by using the visible light irradiator (Power Light manufactured by Tokuyama Dental Co.) for 20 seconds, respectively, to prepare adhesion test pieces.

After the adhesion test pieces were dipped in water of 37° C. for 24 hours, a round stainless steel wire of 0.50 mm was loop-coupled to the bracket wing, and was pulled by using a tension tester (Autograph, manufactured by Shimazu Mfg. Co.) at a cross head speed of 2 mm/min. to measure the tensile adhesive strength between the teeth and the bracket for correction. Four test pieces were measured for their tensile adhesive strength by the above method for each testing, and an average value thereof was regarded to be the strength of adhering the bracket for correcting irregular teeth.

Method of Evaluating Preservation Stability

The adhesive compositions after the preparation were preserved in an incubator maintained at 37° C. for one month. The preserved compositions were measured for their adhesive strengths by the same method as the above method of measuring adhesive strengths, and were compared with the adhesive strengths (initial adhesive strengths) of the compositions of before being preserved at 37° C.

Method of Measuring the Amount of Polyvalent Metal Ions

An adhesive composition was prepared by blending various components together and was stirred for 24 hours. Thereafter, 0.2 g of the adhesive composition was weighed into a 100-ml sampling tube and was diluted into 1% by using an isopropanol. By using an ICP (induction-coupled plasma) emission spectroscopy, the diluted solution was measured for the concentrations (mmols/g) of Al, La and Ca ions per a gram of the polymerizable monomer component (A). Upon calculating the sum of the thus obtained ion concentrations multiplied by the respective ionic valencies, the amount of ionic crosslinking was found, i.e., the amount of polyvalent metal ions (meq) was found per gram of the component (A).

The multivalent metal ions eluting out from the filler used in Experimental Examples (I) and (II) were all Al, La and Ca ions, but contained no other ions.

Preparation Example 1

Preparation of Polyvalent Metal Filler MF1

A fluoroaluminosilicate glass powder (Tokuso Ionomer, manufactured by Tokuyama Dental Co.) was pulverized by using a wet-type continuous ball mill (New My Mill, manufactured by Mitsui Kozan Co.) to possess an average particle size of 0.5 μm. By using 20 g of 5.0 N hydrochloric acid per gram of the obtained powder, the surfaces of the particles were treated for 40 minutes to obtain a polyvalent metal filler (polyvalent metal ion-eluting filler) MF1.

0.1 Gram of the obtained polyvalent metal filler MF1 was maintained dipped in 10 ml of an aqueous solution maintained at 23° C. and containing 10% by weight of maleic acid for 24 hours, and the amount of the eluted polyvalent metal ions was analyzed by using the ICP (induction-coupled plasma) emission spectroscopy to find that the amount of ions eluted out from the polyvalent metal filler MF1 in 24 hours was 10 meq/g—filler.

Preparation Example 2

Preparation of Polyvalent Metal Filler MF2

A multivalent metal filler MF2 was obtained in quite the same manner as in Preparation Example 1 but conducting the treatment with 5.0 N hydrochloric acid for 20 minutes. As a result of the ICP emission spectroscopy, the amount of ions eluted out from the polyvalent metal filler MF2 in 24 hours was 25 meq/g—filler.

Preparation Example 3

Preparation of Polyvalent Metal Filler MF3

A multivalent metal filler MF3 was obtained in quite the same manner as in Preparation Example 1 (or Preparation Example 2) but without at all conducting the treatment with hydrochloric acid. As a result of the ICP emission spectroscopy, the amount of ions eluted out from the polyvalent metal filler MF3 in 24 hours was 50 meq/g—filler.

Preparation Example 4

Preparation of an Adhesive for Composite Resin and Bracket

To a mixed solution of 6.0 g of a polymerizable monomer (BisGMA) and 4.0 g of a triethylene glycol dimethacrylate (3G), were added 0.03 g of a camphor quinone (CQ), 0.05 g of an ethyl p-N,N-dimethylaminobenzoate (DMBE), a polymerization inhibitor [0.01 g of a hydroquinonemonomethyl ether (HQME) and 0.003 g of a 2,6-di-t-butyl-p-cresol (BHT)]. The mixture was stirred in a dark place until becoming homogeneous to prepare a matrix.

3.8 Grams of the thus obtained matrix and 6.2 g of the amorphous silica (F1) were mixed together in an agate mortar, and were defoamed in vacuum to obtain a photocurable composite resin CR1 having a filler-filling rate of 62%. The composition was as shown in Table 1.

Similarly, composite resins CR2 to CR9 were prepared having composition ratios shown in Table 1.

By using the compositions shown in Table 1, further, adhesives OB1 to OB4 for bracket were prepared in the same manner as described above.

The thus prepared adhesives for composite resin and for correction were all preserved in a light-shielding container.

TABLE 1

| | Composite of Matrix[1] | | |
|---|---|---|---|
| | Polymerizable monomer (mass) | Polymerization initiator (mass) | Filler (Filling ratio) |
| CR1 | BisGMA(60)3G(40) | CQ(0.5)DMBE(0.5) | F1(62) |
| CR2 | BisGMA(60)3G(40) | CQ(0.5)DMBE(0.5) | F1(80) |
| CR3 | D26E(60)3G(40) | CQ(0.5)DMBE(0.5) | F1(62) |
| CR4 | BisGMA(54)3G(36)HEMA(10) | CQ(0.5)DMBE(0.5) | F1(62) |
| CR5 | BisGMA(60)3G(40) | CQ(0.5)DMPT(0.5) | F1(62) |
| CR6 | BisGMA(60)3G(40) | CQ(0.3)DMBE(0.5)TPO(0.5) | F1(62) |
| CR7 | BisGMA(60)3G(40) | BDTPO(0.5)DMBE(0.5) | F1(62) |
| CR8 | BisGMA(60)3G(40) | CQ(0.3)DMBE(0.3)MDEOA(0.3)TAZ(0.2) | F1(62) |
| CR9 | BisGMA(60)3G(40) | CQ(0.3)DMBE(0.3)MDEOA(0.3)IMDPI(0.2) | F1(62) |
| OB1 | BisGMA(60)3G(40) | CQ(0.5)DMBE(0.5) | F3(70) |
| OB2 | BisGMA(54)3G(36)HEMA(10) | CQ(0.5)DMBE(0.5) | F3(70) |
| OB3 | BisGMA(54)3G(36)PM(10) | CQ(0.3)DMBE(0.5)TPO(0.5) | F3(70) |
| OB4 | BisGMA(60)3G(40) | CQ(0.5)DMBE(0.5) | F3:MF2 = 8:2(70) |

[1]Containing 0.1 parts by mass of HQME and 0.03 parts by mass of BHT.

Experimental Example (I)

Experiments in the following Experimental Example (I) are to evaluate the adhesive compositions of the invention when they are used as the materials for pre-treating the teeth.
Experiment No. 1
Recipe:
  Polymerizable monomer (A1): 3.0 g of PM
  Polymerizable monomer (A2): 2.4 g of BisGMA
    1.6 g of 3G
    3.0 g of HEMA
  Polyvalent metal filler (B): 1.5 g of MF1
  Water-soluble organic solvent (C):
    8.5 g of isopropanol (IPA)
  Component (D): 2.0 g of distilled water
  Other components: 0.003 g of BHT (polymerization inhibitor)

The above components were stirred and mixed for not less than 3 hours to prepare an adhesive composition for use as the pre-treating material.

By using CR1 as the composite resin, the adhesive composition obtained above was measured for its strength of adhering the composite resin (strength of adhesion to the enamel and the strength of adhesion to the dentin). To evaluate the preservation stability, further, the adhesive composition was preserved in an incubator maintained at 37° C. for one month to measure the strength of adhesion to the enamel and to the dentin.

Table 2 shows the above adhesive composition and Table 3 shows the evaluated results.

In Table 3, X is a value representing the amount of the eluted polyvalent metal ions per gram of the component (A). Experiments Nos. 2 to 26 and Comparative Experiments Nos. 1 to 7

In Experiments Nos. 2 to 26, adhesive compositions shown in Table 2 were prepared in compliance with the method of Experiment No. 1, and were evaluated in the same manner as in Experiment No. 1. The results were as shown in Table 3.

In Comparative Experiments Nos. 1 to 7, the adhesive compositions shown in Table 4 were prepared in compliance with the method of Experiment No. 1, and were evaluated in the same manner as in Experiment No. 1. The results were as shown in Table 5.

TABLE 2

| Expt. No. | Component A A1 | Component A A2 | Component B | Component C | Component D | Others |
|---|---|---|---|---|---|---|
| 1 | PM(30) | BisGMA(24), 3G(16), HEMA(30) | MF1(15) | IPA(85) | water(20) | |
| 2 | PM(30) | BisGMA(24), 3G(16), HEMA(30) | MF2(10) | IPA(85) | water(20) | |
| 3 | PM(30) | BisGMA(24), 3G(16), HEMA(30) | MF2(10) | IPA(85) | water(20) | |
| 4 | PM(30) | BisGMA(24), 3G(16), HEMA(30) | MF2(10) | IPA(85) | water(20) | |
| 5 | PM(30) | BisGMA(24), 3G(16), HEMA(30) | MF2(10) | IPA(85) | water(20) | |
| 6 | PM(30) | BisGMA(24), 3G(16), HEMA(30) | MF2(10) | IPA(85) | water(20) | |
| 7 | PM(30) | BisGMA(24), 3G(16), HEMA(30) | MF2(10) | IPA(85) | water(20) | |
| 8 | PM(30) | BisGMA(24), 3G(16), HEMA(30) | MF2(10) | IPA(85) | water(20) | |
| 9 | PM(30) | BisGMA(24), 3G(16), HEMA(30) | MF2(10) | IPA(85) | water(20) | |
| 10 | PM(30) | BisGMA(24), 3G(16), HEMA(30) | MF2(10) | IPA(85) | water(20) | |
| 11 | PM(30) | BisGMA(24), 3G(16), HEMA(30) | MF3(10) | IPA(85) | water(20) | |
| 12 | PM(30) | BisGMA(24), 3G(16), HEMA(30) | MF2(10) | acetone(85) | water(20) | |
| 13 | PM(30) | BisGMA(24), 3G(16), HEMA(30) | MF2(10) | EtOH(85) | water(20) | |
| 14 | MDP(50) | BisGMA(24), 3G(16), HEMA(30) | MF2(10) | IPA(85) | water(20) | |
| 15 | PM(20), MAC-10(10) | BisGMA(24), 3G(16), HEMA(30) | MF2(10) | IPA(85) | water(20) | |
| 16 | PM(20), 4-META(10) | BisGMA(24), 3G(16), HEMA(30) | MF2(10) | IPA(85) | water(20) | |
| 17 | PM(30) | D26E(40), HEMA(30) | MF2(10) | IPA(85) | water(20) | |
| 18 | PM(30) | MMA(40), HEMA(30) | MF2(10) | IPA(85) | water(20) | |
| 19 | PM(30) | AAEM(40), HEMA(30) | MF2(10) | IPA(85) | water(20) | |
| 10 | PM(30) | BisGMA(24), 3G(16), HEMA(30) | MF2(10) | IPA(55) | water(20) | |
| 21 | PM(30) | BisGMA(24), 3G(16), HEMA(30) | MF2(10) | IPA(140) | water(20) | |
| 22 | PM(10) | BisGMA(24), 3G(16), HEMA(30) | MF2(10) | IPA(85) | water(20) | |
| 23 | PM(50) | HEMA(50) | MF2(10) | IPA(85) | water(20) | |
| 24 | PM(50) | HEMA(50) | MF2(10) | IPA(85) | water(20) | F1(5) |
| 25 | PM(30) | BisGMA(24), 3G(16), HEMA(30) | MF2(10) | IPA(85) | water(20) | F1(5) |
| 26 | PM(30) | BisGMA(24), 3G(16), HEMA(30) | MF2(10) | IPA(85) | water(20) | F1(15) |

[1] Contains 0.03 parts by mass of BHT.

TABLE 3

| Expt. No. | Necessary Amount of ions[1] meq | Necessary amount of solvent[2] 20X | Added amount of solvent | CR | Adhesive strength/MPa (standard deviation) Initial Enamel | Initial Dentin | After preserved at 37° C. for 1 month Enamel | After preserved at 37° C. for 1 month Dentin |
|---|---|---|---|---|---|---|---|---|
| 1 | 1.5 | 30 | 85 | CR1 | 16.2(3.2) | 13.3(2.8) | 12.2(1.2) | 11.3(2.1) |
| 2 | 2.5 | 50 | 85 | CR1 | 17.3(3.1) | 14.5(3.1) | 13.3(3.3) | 11.5(4.1) |
| 3 | 2.5 | 50 | 85 | CR2 | 16.1(4.1) | 13.7(4.1) | 13.1(4.1) | 11.9(2.3) |
| 4 | 2.5 | 50 | 85 | CR3 | 16.3(1.2) | 14.1(3.4) | 13.3(1.2) | 10.9(2.4) |
| 5 | 2.5 | 50 | 85 | CR4 | 18.2(3.5) | 16.3(1.3) | 14.0(3.1) | 11.9(1.0) |
| 6 | 2.5 | 50 | 85 | CR5 | 15.3(4.0) | 12.3(2.5) | 11.9(3.5) | 10.0(2.1) |
| 7 | 2.5 | 50 | 85 | CR6 | 18.1(5.3) | 14.8(1.9) | 15.0(3.8) | 13.2(1.5) |
| 8 | 2.5 | 50 | 85 | CR7 | 18.6(1.2) | 15.1(3.2) | 16.6(1.3) | 13.2(1.1) |
| 9 | 2.5 | 50 | 85 | CR8 | 16.5(4.1) | 13.9(1.8) | 14.5(3.0) | 11.3(2.6) |
| 10 | 2.5 | 50 | 85 | CR9 | 16.1(2.9) | 13.8(3.1) | 13.0(1.9) | 11.8(1.9) |
| 11 | 5 | 100 | 120 | CR1 | 19.9(3.5) | 18.1(4.3) | 17.9(3.1) | 14.3(4.3) |
| 12 | 2.5 | 50 | 85 | CR1 | 17.2(1.2) | 14.1(1.1) | 15.2(3.2) | 12.1(3.1) |
| 13 | 2.4 | 48 | 85 | CR1 | 17.8(3.3) | 14.6(3.2) | 15.1(3.9) | 12.1(3.1) |
| 14 | 2.4 | 48 | 85 | CR1 | 17.3(2.2) | 15.3(2.6) | 14.0(2.8) | 13.3(2.5) |
| 15 | 2.4 | 48 | 85 | CR1 | 17.0(5.2) | 17.3(2.1) | 14.1(3.3) | 15.3(1.3) |
| 16 | 2.4 | 48 | 85 | CR1 | 16.4(3.5) | 16.3(2.9) | 13.3(3.19) | 14.2(2.0) |
| 17 | 2.5 | 50 | 85 | CR1 | 16.2(3.2) | 13.1(2.9) | 14.0(2.2) | 11.3(1.5) |
| 18 | 2.5 | 50 | 85 | CR1 | 19.3(4.1) | 17.5(3.0) | 17.5(3.1) | 15.3(2.1) |
| 19 | 2.5 | 50 | 85 | CR1 | 19.1(2.1) | 18.5(3.5) | 17.7(4.0) | 16.8(3.3) |
| 20 | 2.5 | 50 | 55 | CR1 | 16.4(3.2) | 14.3(2.8) | 14.3(1.2) | 12.3(3.2) |
| 21 | 2.4 | 48 | 140 | CR1 | 17.1(2.2) | 15.2(1.0) | 15.5(1.3) | 12.9(3.4) |
| 22 | 2.4 | 48 | 85 | CR1 | 15.3(4.1) | 15.2(3.3) | 13.1(4.1) | 12.2(3.8) |
| 23 | 2.5 | 50 | 85 | CR1 | 21.0(1.3) | 17.5(3.9) | 20.3(2.5) | 16.9(2.2) |

TABLE 3-continued

| | Necessary | | | | Adhesive strength/MPa (standard deviation) | | | |
| | | | | | Initial | | After preserved at 37° C. for 1 month | |
| Expt. No. | Amount of ions[1] meq | amount of solvent[2] 20X | Added amount of solvent | CR | Enamel | Dentin | Enamel | Dentin |
|---|---|---|---|---|---|---|---|---|
| 24 | 2.5 | 50 | 85 | CR1 | 22.1(2.3) | 18.1(1.1) | 20.5(2.4) | 17.4(2.4) |
| 25 | 2.4 | 48 | 85 | CR1 | 23.3(2.1) | 16.2(1.8) | 21.0(1.0) | 15.2(1.2) |
| 26 | 2.4 | 48 | 85 | CR1 | 22.5(2.8) | 17.3(2.3) | 22.0(1.0) | 16.2(1.2) |

[1]Amount of polyvalent metal ions (meq) eluted in the primer per gram of the component A.
[2]Minimum amount (parts by mass) of the volatile organic solvent necessary for preserving the primer as one solution.

TABLE 4

| Comp. Expt. No. | Primer composition (parts by mass)[1] | | | | | |
| | Component A | | | | | |
| | A1 | A2 | Component B | Component C | Component D | Others |
|---|---|---|---|---|---|---|
| 1 | PM(30) | BisGMA(24), 3G(16), HEMA(30) | — | IPA(85) | water(20) | |
| 2 | PM(30) | BisGMA(24), 3G(16), HEMA(30) | MF2(2) | IPA(85) | water(20) | |
| 3 | PM(30) | BisGMA(24), 3G(16), HEMA(30) | MF3(20) | IPA(85) | water(20) | |
| 4 | PM(30) | BisGMA(24), 3G(16), HEMA(30) | MF2(10) | IPA(35) | water(20) | |
| 5 | PM(30) | BisGMA(24), 3G(16), HEMA(30) | MF2(10) | IPA(170) | water(20) | |
| 6 | PM(30) | BisGMA(30), 3G(20), HEMA(47) | MF2(10) | IPA(85) | water(20) | |
| 7 | PM(30) | BisGMA(24), 3G(16), HEMA(30) | — | IPA(85) | water(20) | F1(5) |

[1]Contains 0.03 parts by mass of BHT.

TABLE 5

| | Necessary | | | | Adhesive strength/MPa (standard deviation) | | | |
| | | | | | Initial | | After preserved at 37° C. for 1 month | |
| Comp. Expt. No. | Amount of ions[1] meq | amount of solvent[2] 20X | Added amount of solvent | CR | Enamel | Dentin | Enamel | Dentin |
|---|---|---|---|---|---|---|---|---|
| 1 | — | — | 85 | CR1 | 10.1(3.5) | 1.9(1.3) | 2.5(1.2) | 1.0(0.2) |
| 2 | 0.5 | 10 | 85 | CR1 | 13.2(2.2) | 7.1(3.1) | 10.1(3.2) | 4.5(3.1) |
| 3 | 9.9 | 198 | 85 | CR1 | 20.8(3.3) | 17.6(3.2) | primer gelled | primer gelled |
| 4 | 2.4 | 48 | 35 | CR1 | 17.3(2.2) | 15.3(2.6) | primer gelled | primer gelled |
| 5 | 2.4 | 48 | 170 | CR1 | 17.0(5.2) | 8.3(2.1) | 13.1(3.3) | 4.1(1.1) |
| 6 | 2.4 | 48 | 85 | CR1 | 5.4(3.5) | 2.3(1.9) | 1.8(1.1) | 1.2(2.0) |
| 7 | — | — | 85 | CR1 | 10.5(3.5) | 2.9(1.3) | 2.5(1.2) | 1.3(0.5) |

[1]Amount of polyvalent metal ions (meq) eluted in the primer per gram of the component A.
[2]Minimum amount (parts by mass) of the volatile organic solvent necessary for preserving the primer as one solution.

In Experiments Nos. 1 to 26, the components were so blended as to satisfy the conditions of the adhesive compositions of the invention. In all cases, favorable adhesive strengths were obtained for the enamel and the dentin. Even after preserved in the incubator at 37° C. for one month, the compositions were not gelled, the adhesive property to the dentin was maintained, and good preservation stability was obtained.

In Comparative Experiment No. 1, on the other hand, no polyvalent metal filler (B) was blended. In Comparative Experiment No. 2, the polyvalent metal filler (B) was blended but the amount of ion elution was not satisfying the conditions of the invention. In either case, therefore, the force of adhesion to the dentin was not sufficient, and the adhesive force greatly decreased after preserved at 37° C. for one month.

In Comparative Experiments Nos. 3 and 4, the amount of blending the volatile water-soluble organic solvent (C) was not satisfying the condition of the invention (blending amount a was smaller than 20·X). Therefore, though the initial strength of adhesion to the dentin was favorable, the compositions were gelled when one to five days have passed after left to stand at 37° C.

In Comparative Experiment No. 5, the volatile water-soluble organic solvent (C) was blended in an amount in excess of the conditions (30 to 150 parts by mass) of the invention, and the strength of adhesion to the dentin was not obtained to a sufficient degree.

In Comparative Experiment No. 6, the blended amount of the volatile water-soluble organic solvent (C) was satisfying the conditions of the invention but the content of the acidic group-containing polymerizable monomer (A1) was not satisfying the conditions of the invention. Therefore, the strength of adhesion was not sufficient to both the enamel and the dentin.

In Comparative Experiment No. 7, no multivalent metal filler (B) was blended but, instead, the inorganic filler that does not elute metal ions was blended. However, the strength of adhesion to the dentin was not sufficient, and the adhesive force greatly decreases after preserved at 37° C. for one month.

Experiments Nos. 27 to 32 and Comparative Experiments Nos. 8 and 9

The adhesive compositions described in Table 6, i.e., the adhesives for the bracket prepared in Preparation Example 4, were evaluated for their strength of adhering the bracket for correcting irregular teeth immediately after the adhesive compositions were prepared and for their strength of adhering the bracket for correcting irregular teeth after the pre-treating materials were preserved in the incubator maintained at 37° C. for one month. The evaluated results were as shown in Table 6.

TABLE 6

| Experiment No. | Primer | Adhesive for correction | Adhesive strength/MPa (Standard deviation) | |
|---|---|---|---|---|
| | | | Initial | After preserved at 37° C. for one month |
| 27 | same as Exp. No. 2 | OB1 | 18.0(3.5) | 16.9(3.1) |
| 28 | same as Exp. No. 2 | OB2 | 18.2(1.2) | 15.2(3.2) |
| 29 | same as Exp. No. 2 | OB3 | 19.1(3.3) | 16.1(3.9) |
| 30 | same as Exp. No. 2 | OB4 | 18.3(2.2) | 15.0(2.8) |
| 31 | same as Exp. No. 18 | OB1 | 19.0(5.2) | 14.1(3.3) |
| 32 | same as Exp. No. 23 | OB1 | 20.4(3.5) | 15.3(3.1) |
| Comp. Experiment 8 | same as Comp. Exp. 1 | OB1 | 12.3(3.2) | 3.0(2.2) |
| Comp. Experiment 9 | same as Comp. Exp. 6 | OB1 | 9.3(4.1) | 5.5(3.1) |

Experiments Nos. 27 to 32 were to evaluate the adhesive compositions prepared by using the components that were satisfying the conditions of the invention. In all cases, there were obtained large strengths of adhering the bracket for correction. The adhesive property was maintained even after preserved in the incubator at 37° C. for one month, and a good preservation stability was obtained.

Comparative Experiment No. 8, on the other hand, was to evaluate the composition of Comparative Experiment No. 1. The adhesive strength greatly decreased after preserved in the incubator at 37° C. for one month. In Comparative Experiment No. 9, the adhesive strength was not obtained to a sufficient degree like in Comparative Experiment No. 6.

Experimental Example (II)

Experiments in the following Experimental Example (II) are to evaluate the adhesive compositions of the invention when they are used as dental adhesives.

Experiment No. 1

Recipe:
 Polymerizable monomer (A1): 1.5 g of PM
 Polymerizable monomer (A2): 5.0 g of D26E
 3.0 g of HEMA
 Polyvalent metal filler (B): 1.5 g of MF2
 Water-soluble organic solvent (C):
 5.0 g of acetone
 Component (D): 1.5 g of distilled water
 Polymerization initiator (E): 0.1 g of CQ
 Other components: 0.15 g of DMBE The above components were stirred and mixed for not less than 3 hours to prepare an adhesive composition for use as the dental adhesive.

In order to measure the thus obtained adhesive composition for its initial strength for adhering the composite resin (strength of adhesion to the enamel and strength of adhesion to the dentin) and to evaluate the preservation stability, the adhesive composition was preserved in the incubator at 37° C. for one month and was measured for its strength of adhesion to the enamel and to the dentin.

Table 7 shows the adhesive composition and Table 8 shows the evaluated results.

In Table 9, X is a value representing the amount of the eluted polyvalent metal ions per gram of the component (A).

Experiments Nos. 2 to 28 and Comparative Experiments Nos. 1 to 19

In Experiments Nos. 2 to 28, adhesive compositions shown in Table 7 and Table 8 were prepared in compliance with the method of Experiment No. 1, and were evaluated in the same manner as in Experiment No. 1. The results were as shown in Table 9 and Table 10.

In Comparative Experiments Nos. 1 to 19, the adhesive compositions shown in Table 11 were prepared in compliance with the method of Experiment No. 1, and were evaluated in the same manner as in Experiment No. 1. The results were as shown in Table 12.

TABLE 7

| Adhesive composition/ parts by mass | Experiment No. | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| Component A | | | | | | | | | | | | | | | | |
| (A1) | | | | | | | | | | | | | | | | |
| PM | 15 | 15 | 15 | 15 | 15 | | 15 | 15 | 15 | 15 | 25 | 25 | 25 | 25 | 25 | 25 |
| MDP | | | | | | 15 | | | | | | | | | | |
| MAC-10 | | | | | | | 10 | | | | | | | | | |
| 4-META | | | | | | | | 10 | | | | | | | | |
| (A2) | | | | | | | | | | | | | | | | |
| D26E | 50 | 50 | 50 | 50 | 50 | 50 | 40 | 40 | 50 | 50 | 50 | | | | | |
| BisGMA | | | | | | | | | | | | 30 | 30 | 30 | 30 | 30 |
| 3G | | | | | | | | | | | | 20 | 20 | 20 | 20 | 20 |
| HEMA | 35 | 35 | 35 | 35 | 35 | 35 | 35 | 35 | 35 | 35 | 35 | 25 | 25 | 25 | 25 | 25 |

TABLE 7-continued

| Adhesive composition/ parts by mass | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Component B | | | | | | | | | | | | | | | | |
| F-1 | | | | | | | | | 15 | | | | | | | |
| F-2 | 10 | 10 | 10 | 10 | 20 | 10 | 10 | 10 | | | 10 | 10 | 10 | 10 | 10 | 10 |
| F-3 | | | | | | | | | | 8 | | | | | | |
| Component C | | | | | | | | | | | | | | | | |
| Water | 15 | 15 | 15 | 15 | 15 | 15 | 15 | 15 | 15 | 15 | 15 | 15 | 15 | 15 | 15 | 15 |
| Component D | | | | | | | | | | | | | | | | |
| Acetone | 50 | 65 | 85 | 140 | 100 | 85 | 85 | 85 | 50 | 90 | 85 | 85 | | | | |
| EtOH | | | | | | | | | | | | | 85 | | | |
| IPA | | | | | | | | | | | | | | 85 | 85 | 85 |
| Component E | | | | | | | | | | | | | | | | |
| CQ | 1.0 | 1.0 | 1.0 | 1.0 | 1.0 | 1.0 | 1.0 | 1.0 | 1.0 | 1.0 | 1.0 | 1.0 | 1.0 | 1.0 | | 1.0 |
| TPO | | | | | | | | | | | | | | | 1.0 | 1.0 |
| DMBE | 1.5 | 1.5 | 1.5 | 1.5 | 1.5 | 1.5 | 1.5 | 1.5 | 1.5 | 1.5 | 1.3 | 1.5 | 1.5 | 1.5 | | 1.0 |
| Other inorganic fillers | | | | | | | | | | | | | | | | |
| Si—Ti | | | | | | | | | | | | | | | | |

TABLE 8

| Adhesive composition/ parts by mass | 17 | 18 | 19 | 20 | 21 | 22 | 23 | 24 | 25 | 26 | 27 | 28 |
|---|---|---|---|---|---|---|---|---|---|---|---|---|
| Component A (A1) | | | | | | | | | | | | |
| PM | 25 | 45 | 10 | 15 | 15 | 15 | 15 | 15 | 15 | 15 | 25 | 25 |
| MDP | | | | | | | | | | | | |
| MAC-10 | | | | | | | | | | | | |
| 4-META | | | | | | | | | | | | |
| (A2) | | | | | | | | | | | | |
| D26E | | 35 | 35 | 50 | 50 | 50 | 50 | 50 | 50 | 50 | | |
| BisGMA | 30 | | | | | | | | | | 30 | 30 |
| 3G | 20 | | | | | | | | | | 20 | 20 |
| HEMA | 25 | 20 | 20 | 35 | 35 | 35 | 35 | 35 | 35 | 35 | 35 | 35 |
| Component B | | | | | | | | | | | | |
| F-1 | | | | 17 | | | | | | | | |
| F-2 | 10 | 10 | 10 | | | 10 | 10 | 5 | | 10 | 10 | 10 |
| F-3 | | | | | 3 | | | | 12 | | | |
| Component C | | | | | | | | | | | | |
| Water | 15 | 15 | 15 | 15 | 15 | 5 | 25 | 15 | 15 | 15 | 15 | 15 |
| Component D | | | | | | | | | | | | |
| Acetone | 85 | 85 | 85 | 85 | 85 | 85 | 85 | 35 | 140 | 55 | 85 | 85 |
| EtOH | | | | | | | | | | | | |
| IPA | | | | | | | | | | | | |
| Component E | | | | | | | | | | | | |
| CQ | 4.0 | 1.0 | 1.0 | 1.0 | 1.0 | 1.0 | 1.0 | 1.0 | 1.0 | 1.0 | 1.0 | 1.0 |
| TPO | | | | | | | | | | | | |
| DMBE | 4.0 | 1.5 | 1.5 | 1.5 | 1.5 | 1.5 | 1.5 | 1.5 | 1.5 | 1.5 | 1.5 | 1.5 |
| Other inorganic fillers | | | | | | | | | | | | |
| Si—Ti | | | | | | | | | | 10 | 10 | 20 |

TABLE 9

| Expt. No. | Amount of ions[1] X meq | Necessary amount of solvent[2] 20X | Added amount of solvent | Initial adhesive strength Enamel | Initial adhesive strength Dentin | After preserved at 37° C. for 1 month Enamel | After preserved at 37° C. for 1 month Dentin |
| --- | --- | --- | --- | --- | --- | --- | --- |
| 1  | 2.4 | 48 | 50  | 15.7(3.2) | 14.8(4.1) | 11.8(2.1) | 10.9(2.9) |
| 2  | 2.4 | 48 | 65  | 21.7(2.9) | 20.1(3.6) | 19.4(2.1) | 19.0(1.8) |
| 3  | 2.4 | 48 | 85  | 22.7(2.9) | 21.1(3.6) | 21.8(2.1) | 20.8(1.8) |
| 4  | 2.4 | 48 | 140 | 14.6(2.2) | 15.2(3.3) | 14.1(2.9) | 14.5(2.1) |
| 5  | 4.6 | 92 | 100 | 16.8(3.2) | 17.5(2.0) | 12.3(3.0) | 12.0(4.2) |
| 6  | 2.2 | 44 | 85  | 18.2(2.2) | 19.0(3.3) | 17.6(3.2) | 18.6(2.3) |
| 7  | 2.6 | 52 | 85  | 21.2(2.8) | 19.6(2.7) | 19.4(4.2) | 19.5(1.9) |
| 8  | 2.4 | 48 | 85  | 18.8(1.8) | 19.2(1.5) | 18.0(3.0) | 18.4(2.6) |
| 9  | 1.6 | 32 | 50  | 16.5(2.6) | 17.3(2.1) | 16.8(2.5) | 16.2(2.0) |
| 10 | 4.2 | 84 | 90  | 17.0(1.7) | 17.5(3.1) | 13.7(2.2) | 12.8(1.7) |
| 11 | 2.4 | 48 | 85  | 21.0(2.1) | 20.4(1.3) | 20.6(2.1) | 19.8(3.3) |
| 12 | 2.4 | 48 | 85  | 19.8(3.4) | 21.2(4.1) | 19.2(1.4) | 20.7(2.3) |
| 13 | 2.2 | 44 | 85  | 19.3(3.2) | 19.2(2.0) | 18.8(3.2) | 18.0(3.3) |
| 14 | 2.6 | 52 | 85  | 20.2(2.2) | 19.5(3.0) | 19.9(1.9) | 18.2(2.1) |
| 15 | 2.4 | 48 | 85  | 18.9(2.1) | 22.1(3.2) | 18.5(2.8) | 21.6(3.0) |
| 16 | 2.6 | 52 | 85  | 22.3(1.7) | 21.0(2.4) | 21.3(2.9) | 20.5(4.2) |

[1] Amount of polyvalent metal ions (meq) eluted in the adhesive per gram of the component A.
[2] Minimum amount (parts by mass) of the volatile water-soluble organic solvent necessary for preserving the adhesive as one solution.

TABLE 10

| Expt. No. | Amount of ions[1] X meq | Necessary amount of solvent[2] 20X | Added amount of solvent | Initial adhesive strength Enamel | Initial adhesive strength Dentin | After preserved at 37° C. for 1 month Enamel | After preserved at 37° C. for 1 month Dentin |
| --- | --- | --- | --- | --- | --- | --- | --- |
| 17 | 2.6 | 52  | 85  | 16.4(3.0) | 15.8(1.3) | 15.8(3.2) | 14.9(2.1) |
| 18 | 2.4 | 48  | 85  | 15.6(2.2) | 16.3(3.1) | 14.8(1.7) | 15.4(2.8) |
| 19 | 2.6 | 52  | 85  | 14.8(2.1) | 15.6(1.7) | 14.0(1.9) | 14.8(2.2) |
| 20 | 1.4 | 28  | 85  | 17.8(2.1) | 18.6(2.1) | 17.5(2.0) | 19.0(2.2) |
| 21 | 1.4 | 28  | 85  | 18.3(2.0) | 17.9(1.9) | 18.0(2.2) | 18.5(1.8) |
| 22 | 2.2 | 44  | 85  | 14.8(3.2) | 16.8(2.0) | 14.4(1.6) | 15.9(2.2) |
| 23 | 2.4 | 48  | 85  | 15.0(3.2) | 15.2(2.6) | 14.5(1.2) | 15.0(1.8) |
| 24 | 1.5 | 30  | 35  | 16.3(2.9) | 15.8(4.1) | 11.8(1.8) | 10.2(2.2) |
| 25 | 6.1 | 122 | 140 | 15.2(4.0) | 16.2(3.9) | 12.9(3.0) | 11.7(2.0) |
| 26 | 2.4 | 48  | 55  | 21.4(3.1) | 19.7(3.1) | 17.1(3.5) | 16.6(1.6) |
| 27 | 2.1 | 42  | 85  | 19.8(2.2) | 18.9(3.3) | 18.5(2.0) | 17.8(1.4) |
| 28 | 2.3 | 46  | 85  | 20.0(1.5) | 20.5(2.8) | 19.3(2.0) | 18.6(1.7) |

[1] Amount of polyvalent metal ions (meq) eluted in the adhesive per gram of the component A.
[2] Minimum amount (parts by mass) of the volatile water-soluble organic solvent necessary for preserving the adhesive as one solution.

TABLE 11

| Adhesive composition/ parts by mass | Comparative Experiment No. | | | | | | | | | | | | | | | | | | |
| --- | --- | --- | --- | --- | --- | --- | --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 | 13 | 14 | 15 | 16 | 17 | 18 | 19 |
| Component A | | | | | | | | | | | | | | | | | | | |
| (A1) | | | | | | | | | | | | | | | | | | | |
| PM | 15 | 15 | 15 | 15 | 15 | 25 | 25 | 25 |  | 2 | 15 | 15 | 15 | 15 | 15 | 15 | 15 | 15 | 15 |
| (A2) | | | | | | | | | | | | | | | | | | | |
| D26E | 50 | 50 | 50 | 50 | 50 |  | 50 | 50 | 65 | 63 | 50 | 50 | 50 | 50 | 50 | 50 | 50 | 50 | 50 |
| BisGMA |  |  |  |  |  | 30 | 30 | 30 | | | | | | | | | | | |
| 3G |  |  |  |  |  | 20 | 20 | 20 | | | | | | | | | | | |
| HEMA | 35 | 35 | 35 | 35 | 35 | 25 | 25 | 25 | 35 | 35 | 35 | 35 | 35 | 35 | 35 | 35 | 35 | 35 | 35 |

TABLE 11-continued

| Adhesive composition/ parts by mass | Comparative Experiment No. | | | | | | | | | | | | | | | | | | |
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 |
| Component B | | | | | | | | | | | | | | | | | | | |
| F-1 | | | | | 15 | | | | | | | 5 | | | | | | 10 | |
| F-2 | 10 | 10 | 20 | | | 10 | 10 | 10 | 10 | 10 | | | | 10 | 10 | 10 | 10 | | 10 |
| F-3 | | | | 12 | | | | | | | | | 16 | | | | | | |
| Component C | | | | | | | | | | | | | | | | | | | |
| Water | 15 | 15 | 15 | 15 | 15 | 15 | 15 | 15 | 15 | 15 | 15 | 15 | 15 | | 0.5 | 45 | 15 | 15 | 15 |
| Component D | | | | | | | | | | | | | | | | | | | |
| Acetone | 40 | 20 | 60 | 85 | 25 | 40 | | | 85 | 85 | 85 | 85 | 135 | 85 | 85 | 85 | | 25 | 160 |
| EtOH | | | | | | | 40 | | | | | | | | | | | | |
| IPA | | | | | | | | 40 | | | | | | | | | | | |
| Component E | | | | | | | | | | | | | | | | | | | |
| CQ | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| DMBE | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 | 1.5 |

TABLE 12

| Comp. Expt. No. | Necessary Amount of ions[1] meq | Added amount of solvent[2] 20X | amount of solvent | Adhesive strength/MPa (standard deviation) | | | |
|---|---|---|---|---|---|---|---|
| | | | | Initial adhesive strength | | After preserved at 37° C. for 1 month | |
| | | | | Enamel | Dentin | Enamel | Dentin |
| 1 | 2.4 | 48 | 40 | 14.3(4.1) | 13.7(3.0) | X (gelled) | X (gelled) |
| 2 | 2.4 | 48 | 20 | 4.6(1.9) | 3.2(4.2) | X (gelled) | X (gelled) |
| 3 | 4.6 | 92 | 60 | 12.9(2.4) | 14.0(3.3) | X (gelled) | X (gelled) |
| 4 | 6.1 | 122 | 85 | 14.2(3.0) | 15.8(4.0) | X (gelled) | X (gelled) |
| 5 | 1.6 | 32 | 25 | 3.2(2.2) | 4.1(3.2) | X (gelled) | X (gelled) |
| 6 | 2.4 | 48 | 40 | 12.9(3.3) | 15.3(2.8) | X (gelled) | X (gelled) |
| 7 | 2.5 | 50 | 40 | 11.9(2.3) | 13.2(1.8) | X (gelled) | X (gelled) |
| 8 | 2.6 | 52 | 40 | 12.2(1.3) | 14.3(3.1) | X (gelled) | X (gelled) |
| 9 | — | — | 85 | 2.1(1.0) | 3.2(1.8) | 1.2(0.6) | 2.2(1.2) |
| 10 | 2.4 | 48 | 85 | 5.3(2.0) | 6.3(1.2) | 4.0(2.2) | 3.2(2.1) |
| 11 | — | — | 85 | 6.3(2.0) | 9.2(3.3) | 4.8(3.1) | 7.4(2.8) |
| 12 | 0.5 | 10 | 85 | 9.5(2.8) | 10.0(2.9) | 8.5(2.2) | 9.2(4.3) |
| 13 | 8.1 | 162 | 170 | 7.5(1.8) | 9.0(1.9) | 6.4(2.2) | 8.2(2.3) |
| 14 | — | — | 85 | 3.0(1.2) | 2.9(1.0) | 1.8(1.0) | 2.0(1.2) |
| 15 | 2 | 40 | 85 | 4.7(2.0) | 4.3(1.2) | 3.8(2.2) | 3.8(1.9) |
| 16 | 2.2 | 44 | 85 | 5.2(2.1) | 6.3(1.9) | 4.3(2.1) | 5.2(2.2) |
| 17 | 2.2 | 44 | 0 | 3.8(2.2) | 4.0(3.0) | X (gelled) | X (gelled) |
| 18 | 1 | 20 | 25 | 3.4(1.2) | 2.9(0.3) | 2.2(1.0) | 1.9(0.2) |
| 19 | 2.4 | 48 | 160 | 3.8(2.2) | 4.0(3.0) | 2.8(1.2) | 2.6(0.8) |

[1]Amount of polyvalent metal ions (meq) eluted in the adhesive per gram of the component A.
[2]Minimum amount (parts by mass) of the volatile water-soluble organic solvent necessary for preserving the adhesive as one solution.

In the adhesive compositions of Experiments Nos. 1 to 28, the components are so blended as to satisfy the conditions of the invention. In all cases, there were obtained favorable strengths of adhesion to the enamel and to the dentin. Even when preserved in the incubator at 37° C. for one month, the adhesives were not gelled but maintained adhesive property to the dentin and favorable preservation stability.

On the other hand, Comparative Experiments Nos. 1 to 8 were the cases where the blended amounts of the volatile water-soluble organic solvent (C) were not satisfying the conditions specified by the invention ($\alpha$<20X). The initial strengths of adhesion to the dentin was favorable immediately after the preparation. However, the adhesives were gelled when one to five days have passed after left to stand at 37° C.

In Comparative Experiment No. 9, no acidic group-containing polymerizable monomer (A1) was blended. In Comparative Experiment No. 10, the amount of the acidic group-containing polymerizable monomer (A1) in the monomer component (A) was less than 5% by mass. In either case, therefore, the power for deliming the dentin was insufficient, and the adhesive force was low.

In Comparative Experiment No. 11, no polyvalent metal filler (B) was blended. In Comparative Experiment No. 12, the polyvalent metal filler (B) was blended but the polyvalent metal ions eluted out in small amounts. In either case, therefore, the ionic crosslinking was insufficient, and the strengths of adhesion to the dentin were low.

In Comparative Experiment No. 13, the polyvalent metal ions eluted out in too large amounts causing a decrease in the power for deliming the dentin. Besides, the volatile organic solvent (C) was necessary in an increased amount for preserving the adhesive composition in the form of one liquid. This caused a shortage of the effective component that formed the adhesive layer after blown with the air, and the adhesive strength decreased.

In Comparative Experiment No. 14, no water (D) was blended. In Comparative Experiment No. 15, water (D) was blended in a small amount. In either case, therefore, the power for deliming the dentin was insufficient, and the adhesive strength was small. In Comparative Experiment No. 16, water (D) was blended in a too large amount. However, the adhesive itself lacked the strength, and the adhesive strength was low.

Comparative Experiment No. 17 was a case where no volatile water-soluble organic solvent (C) was added. In this case, however, permeability to the dentin was insufficient and, therefore, the initial adhesive strength was low. Besides, the composition was gelled when one to five days have passed after left to stand at 37° C. Further, Comparative Experiment No. 18 was a case where the volatile organic solvent was added in a small amount (less than 30 parts by mass). In this case, permeability to the dentin insufficient and, therefore, the adhesive strength was low. Further, Comparative Experiment No. 19 was a case where the volatile organic solvent (C) was added in a too large amount. In this case, the effective component that formed the adhesive layer became insufficient after blown with the air, and the adhesive strength was low.

The invention claimed is:

1. A one-package dental adhesive composition comprising:
    (A) a polymerizable monomer component containing not less than 5% by mass of an acidic group-containing polymerizable monomer;
    (B) a polyvalent metal ion-eluting filler;
    (C) a volatile organic solvent;
    (D) water; and
    (E) a photopolymerization initiator,
    wherein said polyvalent metal ion-eluting filler (B) is blended in such an amount that the amount of the polyvalent metal ions eluted out from said filler becomes 1.0 to 7.0 meq per gram of said polymerizable monomer component (A);
    said volatile organic solvent (C) is blended in an amount in a range of 60 to 100 parts by mass per 100 parts by mass of said polymerizable monomer component (A) satisfying a condition expressed by the following formula (1):
    $$\alpha \geq 20 \cdot X \quad (1)$$
    wherein $\alpha$ is the amount of said volatile organic solvent (C) blended per 100 parts by mass of said polymerizable monomer component (A),
    X is a number representing the amount of the polyvalent metal ions eluted out from said polyvalent metal ion-eluting filler (B) or the amount (meq) thereof per gram of said polymerizable monomer component (A), and
    said water (D) is blended in an amount of 3 to 30 parts by mass per 100 parts by mass of said polymerizable monomer component (A),
    wherein the dental adhesive composition is not gelled after preservation for one month at 37° C.

2. The one-package dental adhesive composition according to claim 1, wherein (F) a polyvalent metal ion non-releasing inorganic filler is, further, contained in an amount of 2 to 20 parts by mass per 100 parts by mass of said polymerizable monomer component (A).

3. The one-package dental adhesive composition according to claim 1, wherein the acidic group-containing polymerizable monomer in said polymerizable monomer component (A) is a polymerizable monomer containing a phosphoric acid group.

4. The one-package dental adhesive composition according to claim 1, wherein said polyvalent metal ion-eluting filler (B) shows the polyvalent metal ion elution amount of 5.0 to 500 meq/g—filler when 0.1 g of said filler is added to 10 ml of an aqueous solution containing 10% by weight of a maleic acid and is held at 23° C. for 24 hours.

5. The one-package dental adhesive composition according to claim 1, wherein said polyvalent metal ion-eluting filler has an average particle size of 0.01 to 5 μm.

* * * * *